(12) United States Patent
Ando

(10) Patent No.: US 7,817,779 B2
(45) Date of Patent: Oct. 19, 2010

(54) NONDESTRUCTIVE ANALYSIS METHOD, NONDESTRUCTIVE ANALYSIS DEVICE, AND SPECIFIC OBJECT ANALYZED BY THE METHOD/DEVICE

(75) Inventor: Masami Ando, 5-13, Koyadai, 2-chome, Tsukuba-shi, Ibaraki (JP)

(73) Assignee: Masami Ando, Tsukuba-shi (JP)

( * ) Notice: Subject to any disclaimer, the term of this patent is extended or adjusted under 35 U.S.C. 154(b) by 175 days.

(21) Appl. No.: 12/073,976

(22) Filed: Mar. 12, 2008

(65) Prior Publication Data

US 2008/0298551 A1 Dec. 4, 2008

Related U.S. Application Data

(63) Continuation of application No. 10/483,399, filed as application No. PCT/JP02/06595 on Jun. 28, 2002, now abandoned.

(30) Foreign Application Priority Data

| Jul. 11, 2001 | (JP) | ............................. 2001-211221 |
| Mar. 4, 2002 | (JP) | ............................. 2002-058053 |
| Jun. 26, 2002 | (JP) | ............................. 2002-186332 |

(51) Int. Cl.
*G01N 23/20* (2006.01)
*G01N 23/207* (2006.01)

(52) U.S. Cl. ............................. 378/71; 378/62; 378/70; 378/84

(58) Field of Classification Search ................ 378/50, 378/53, 62, 70, 71, 73, 76, 84, 85, 86, 87, 378/90; 250/505.1
See application file for complete search history.

(56) References Cited

U.S. PATENT DOCUMENTS 4,884,290 A 11/1989 Tamura et al.

(Continued)

FOREIGN PATENT DOCUMENTS

| JP | 2694049 | 9/1997 |
| JP | 2001-33406 | 2/2001 |

OTHER PUBLICATIONS

An International Search Report issued Jul. 30, 2002 in International Application No. PCT/JP02/06595.

(Continued)

*Primary Examiner*—Allen C. Ho
(74) *Attorney, Agent, or Firm*—Wenderoth, Lind & Ponack, L.L.P.

(57) ABSTRACT

Non-destructive analysis is carried out by irradiating an object with X-rays, for example, so that the X-rays from the object are incident on an analyzer crystal. The analyzer crystal can be of a transmission-type or a reflection-type. A pre-crystal device is used to make the radiation monochromated and parallelized. Atomic lattice planes of the pre-crystal device are approximately parallel with the atomic lattice planes of the analyzer crystal so as to use the angular analysis capability of the analyzer crystal. The thickness of the analyzer crystal is fixed. For example, for a transmission-type analyzer crystal, the thickness is such that irradiation with monochromatic parallel X-rays in the absence of the object results in a condition in which either one of (a) X-rays along a forward diffraction direction and (b) X-rays along a diffraction direction obtained by dynamical diffraction by the transmission type analyzer crystal have an intensity of nearly zero as compared to the intensity of the other with respect to the monochromatic parallel X-rays. At least one or both of an X-ray dark-field image and an X-ray bright-field are obtained.

6 Claims, 15 Drawing Sheets

U.S. PATENT DOCUMENTS

| | | | |
|---|---|---|---|
| 5,245,648 | A | 9/1993 | Kinney et al. |
| 5,319,694 | A | 6/1994 | Ingal et al. |
| 5,509,043 | A | 4/1996 | Van Der Sluis |
| 5,579,363 | A | 11/1996 | Ingal et al. |
| 5,715,291 | A | 2/1998 | Momose |
| 5,802,137 | A | 9/1998 | Wilkins |
| 5,850,425 | A | 12/1998 | Wilkins |
| 5,881,126 | A | 3/1999 | Momose |
| 5,930,325 | A | 7/1999 | Momose |
| 5,987,095 | A | 11/1999 | Chapman et al. |
| 6,574,306 | B2 | 6/2003 | Kikuchi |
| 6,577,708 | B2 | 6/2003 | Chapman et al. |
| 6,870,896 | B2 | 3/2005 | Protopopov |
| 6,873,681 | B2 * | 3/2005 | Toraya et al. ............. 378/71 |
| 6,947,521 | B2 | 9/2005 | Wernick et al. |
| 7,062,015 | B2 * | 6/2006 | Lewis ..................... 378/84 |
| 7,076,025 | B2 | 7/2006 | Hasnah et al. |
| 2006/0056590 | A1 | 3/2006 | Nikulin |

OTHER PUBLICATIONS

U.S. Office Action mailed Jan. 4, 2006 in U.S. Appl. No. 10/483,399.
U.S. Office Action mailed Sep. 28, 2006 in U.S. Appl. No. 10/483,399.
U.S. Office Action mailed Sep. 12, 2007 in U.S. Appl. No. 10/483,399.
Japanese Office Action dated Dec. 21, 2009 in corresponding Japanese Patent Application No. 2002-186332 (with English translation).

* cited by examiner

8(b)

8(a)

NONDESTRUCTIVE ANALYSIS METHOD, NONDESTRUCTIVE ANALYSIS DEVICE, AND SPECIFIC OBJECT ANALYZED BY THE METHOD/DEVICE

This application is a continuation application of Ser. No. 10/483,399, filed May 14, 2004, now ABN, which is the National Stage of International Application No. PCT/JP02/06595, filed Jun. 28, 2002.

BACKGROUND OF THE INVENTION

1. Technical Field

The invention relates to a nondestructive analysis method, a nondestructive analysis device, and a specific object by analyzed the method/device.

2. Background Art

With conventional transmission X-rays, the contrast of a resulting image depends on the magnitude of absorption of the X-rays by the object. Namely, if there is a region where the elements, structures, and densities of substances with high X-ray absorptance are dense, that portion exhibits a low transmittance and can be caught as a dark shadow in an image.

There is also a recently known method of capturing the state of refraction of X-rays dependent on the elements, structures, and densities of substances, not the absorption of X-rays. Monochromatic parallel X-rays have a wave front (X-rays are plane waves) which varies with a phase shift caused by the object. Since the phase shift is equivalent to the amount of change of the wave front form, detecting the phase shift corresponds to detecting the wave front form.

Here, a transmission-type or reflection-type analyzer crystal is used to determine the wave front form. A bend of the wave front of X-rays may be considered as the X-rays being refracted to a different direction of propagation. The propagation direction varies slightly according to the gradient of the wave front.

Considering the situation where an angle of incidence is set so that the transmission-type or reflection-type analyzer crystal satisfies a diffraction condition with respect to the monochromatic parallel X-rays, the transmission-type or reflection-type analyzer crystal's function is to detect a certain gradient part of the wave front. The refraction angle of the X-ray beam is known as a mode for examining the phase shift caused by the object, i.e., the refraction angle of the image, and a phase distribution is determined from the distribution of refraction angles obtained.

To take a specific example of a technology for analyzing the internal structure of an object nondestructively, there have already been various techniques proposed as ways of obtaining an image inside an object by using X-rays, including Japanese Patent No. 2694049.

Here, the object is irradiated with monochromatic X-rays (in reality, the monochromatic X-rays in use refer to X-rays having a distribution on the order of approximately one ten-thousandth in terms of the ratio $\Delta\lambda/\lambda$, where $\Delta\lambda$ is the accompanying distribution of the wavelength $\lambda$ of the monochromatic X-rays), X-rays from the object are introduced to an analyzer crystal (also referred to as crystal analysis plate, crystal analysis device, etc.), and a transmission beam and a diffraction beam emitted from the transmission-type analyzer crystal (technically, based on the case called Laue case) are used to obtain the image inside the object. This utilizes the fact that the analyzer crystal has an angular-analysis capability. The image obtained by the angular-analysis is paired with a similar image having different contrast between the transmission beam and diffraction beam (a reverse image of opposite signs; specifically, a white-and-black image if the other image is black-and-white).

Japanese Patent No. 2694049 describes monochromatic parallel X-rays used with the transmission-type analyzer crystal passing through an object without causing reaction with the object, and the monochromatic parallel X-rays and the refraction X-rays from the object are obtained as a transmission beam and a diffraction beam with mutual superimposition. In this case, an X-ray bright-field image is obtained.

Here, the X-ray bright-field image refers to an image in which signals from the object are superimposed on an illuminated background. In contrast, an X-ray dark-field image refers to an image which consists chiefly of signals from the object with no or a scarcely illuminated background. (Millions of stars in the sky may be taken as an illustration of an X-ray dark-field image.)

Among other examples is U.S. Pat. No. 5,850,425, in which an object is irradiated with monochromatic X-rays, and the refraction X-rays from the object are introduced to an analyzer crystal to utilize reflection X-rays through the Bragg reflection emitted from the analyzer crystal as the reflection-type analyzer crystal (technically, based on the case called the Bragg case). U.S. Pat. No. 5,850,425 describes the monochromatic parallel X-rays used with the reflection-type analyzer crystal passing through an object without causing interaction of the object, and the monochromatic parallel X-rays and the refraction X-rays from the object are reflected with mutual superimposition. This also results in an X-ray bright-field image.

Another technique has also been proposed in which an object is irradiated with monochromatic X-rays, and refraction X-rays from the object are introduced to a pair of reflection-type asymmetric analyzer crystals for double reflection, so that an image distorted by the first reflection is corrected into an undistorted one by the second reflection.

Nevertheless, these conventional nondestructive analysis methods have demonstrated the following problems.

That is, any of the foregoing nondestructive analysis techniques can only obtain poor-contrast, hard-to-recognize images due to the configuration that is chiefly intended to obtain an X-ray bright-field image, or an X-ray image or information on an object, in which the monochromatic X-rays in use pass through the object without causing reaction with the object, and the monochromatic X-rays are superimposed with the refraction X-rays and the like from the object, i.e. superimposed with X-rays affected by the intensity of the X-rays incident directly in the X-ray bright-field image. It has thus been impossible to obtain nothing other than poor-contrast, hard-to-recognize images.

Furthermore, none of the aforementioned describes a method for obtaining an X-ray dark-field image from the resulting X-ray bright-field image.

Moreover, the nondestructive analysis technique of Japanese Patent No. 2694049 has the problem that when the angular-analysis capability of the transmission-type analyzer crystal is utilized, the effect of the wavelength distribution of the monochromatic X-rays remains, or equivalently, an achromatic condition (condition for simultaneous diffraction in all the wavelengths including the accompanying wavelength distribution $\Delta\lambda$ of the wavelength $\lambda$ of the monochromatic X-rays) fails to be satisfied since no consideration is given to parallelization between the atomic lattice planes of the monochromator for generating the monochromatic X-rays and the atomic lattice planes of the analyzer crystal. Furthermore, there is the problem of requiring complicated operations for storing a white-and-black image and a black-and-white image with successive rotations of the transmission-type analyzer crystal and forming a high contrast image through a computer since no consideration is given to forming the transmission-type analyzer crystal of a certain thickness. It is thus impossible to obtain the desired image of the object at one time.

The invention of this application has been achieved in view of the foregoing. Thus, an object of the invention is to solve the problems of the conventional art and provide a new nondestructive analysis method and nondestructive analysis device, as well as a specific object analyzed by the nondestructive analysis method and device, which can realize a configuration chiefly intended to obtain an X-ray dark-field image in particular, or an X-ray image or object information by X-rays, unaffected by the intensities of the directly incident X-rays and the monochromatic X-rays in use, with an elimination or a reduction of an unnecessary illuminated background of X-rays, and can obtain a high-contrast image from inside an object at one time with ease.

Here, the X-ray dark-field image differs from the X-ray bright-field image in that the X-ray dark-field image is made of an object image alone with no or a fractionally scarcely illuminated background, being characterized in that the imaging is possible even with weak object signals alone.

SUMMARY OF THE INVENTION

To solve the foregoing problems, the invention of this application firstly provides a nondestructive analysis method for irradiating an object with monochromatic parallel X-rays, making X-rays from the object incident on a transmission-type analyzer crystal, and obtaining an image inside the object by X-rays emitted from the transmission-type analyzer crystal. The thickness of the transmission-type analyzer crystal is initially set to a thickness such that when there is no object, either ones of X-rays along a forward diffraction direction and X-rays along a diffraction direction obtained by a dynamical diffraction action of the transmission-type analyzer crystal have an intensity of nearly zero as compared to the intensity of the others with respect to the monochromatic parallel X-rays in use. Either one or both of an X-ray dark-field image and an X-ray bright-field image are provided when the X-rays from the object are made incident on this transmission-type analyzer crystal.

In addition, the invention of this application secondly provides a nondestructive analysis method for irradiating an object with monochromatic parallel X-rays, making X-rays from the object incident on a reflection-type analyzer crystal, and obtaining an image inside the object by X-rays emitted from the reflection-type analyzer crystal. The thickness of the reflection-type analyzer crystal is initially set to a thickness such that the X-rays from the object satisfy a diffraction condition and are transmitted by a dynamical diffraction action of the reflection-type analyzer crystal. The reflection-type analyzer crystal reflects the monochromatic parallel X-rays in use with a reduction in X-ray intensity and transmits the X-rays from the object so that an X-ray dark-field image is provided.

In addition, the invention of this application thirdly provides a nondestructive analysis device for irradiating an object with monochromatic parallel X-rays, making X-rays from the object incident on a transmission-type analyzer crystal, and obtaining an image inside the object by X-rays emitted from the transmission-type analyzer crystal. The thickness of the transmission-type analyzer crystal is initially set to a thickness such that when there is no object, either ones of X-rays along a forward diffraction direction and X-rays along a diffraction direction obtained by a dynamical diffraction action of the transmission-type analyzer crystal have an intensity of nearly zero as compared to the intensity of the others with respect to monochromatic parallel X-rays in use. Either one or both of an X-ray dark-field image and an X-ray bright-field image are provided when the X-rays from the object are made incident on the transmission-type analyzer crystal.

According to a further aspect the present invention provides a nondestructive analysis device for irradiating an object with monochromatic parallel X-rays, making X-rays from the object incident on a transmission-type analyzer crystal, and obtaining an image inside the object by X-rays emitted from the transmission-type analyzer crystal. The thickness of the transmission-type analyzer crystal is initially set to a thickness such that when there is no object, either ones of X-rays along a forward diffraction direction and X-rays along a diffraction direction obtained by a dynamical diffraction action of the transmission-type analyzer crystal have an intensity of nearly zero as compared to the intensity of the others with respect to monochromatic parallel X-rays in use. Either one or both of the X-rays along the forward diffraction direction and the X-rays along the diffraction direction are obtained when the X-rays from the object are made incident on the transmission-type analyzer crystal.

According to a fifth aspect the invention provides a nondestructive analysis device for irradiating an object with monochromatic parallel X-rays, making X-rays from the object incident on a transmission-type analyzer crystal, and obtaining an image inside the object by X-rays emitted from the transmission-type analyzer crystal. The transmission-type analyzer crystal is initially shaped so that it periodically exhibits thicknesses such that when there is no object, either one of X-rays along a forward diffraction direction and X-rays along a diffraction direction obtained by a dynamical diffraction action of the transmission-type analyzer crystal have an intensity of nearly zero as compared to the intensity of the other with respect to monochromatic parallel X-rays in use. A slit plate is arranged on an output side of the transmission-type analyzer crystal. When the X-rays from the object are made incident on the transmission-type analyzer crystal, the transmission-type analyzer crystal and the slit plate are moved or the object is moved to obtain a plurality of slit-like images. The images are synthesized into either one or both of an X-ray dark-field image and an X-ray bright-field image.

According to a sixth aspect the invention provides a nondestructive analysis device for irradiating an object with monochromatic parallel X-rays, making X-rays from the object incident on a reflection-type analyzer crystal, and obtaining an image inside the object by X-rays emitted from the reflection-type analyzer crystal. The thickness of the reflection-type analyzer crystal is initially set to a thickness such that the X-rays from the object satisfy a diffraction condition and are transmitted by a dynamical diffraction action of the reflection-type analyzer crystal. The reflection-type analyzer crystal reflects the monochromatic parallel X-rays in use with a reduction in X-ray intensity and transmits the X-rays from the object so that an X-ray dark-field image is provided.

Accordingly to a seventh aspect the present invention provides a nondestructive analysis device for irradiating an object with monochromatic parallel X-rays, making X-rays from the object incident on a reflection-type analyzer crystal, and obtaining an image inside the object by X-rays emitted from the reflection-type analyzer crystal. The thickness of the reflection-type analyzer crystal is initially set to a thickness such that the X-rays from the object satisfy a diffraction condition and are transmitted by a dynamical diffraction action of the reflection-type analyzer crystal. The reflection-type analyzer crystal reflects the monochromatic parallel X-rays in use with a reduction in X-ray intensity and transmits the X-rays from the object so that an image of the X-rays is provided.

According to an eighth aspect the invention provides a nondestructive analysis device for irradiating an object with monochromatic parallel X-rays, making X-rays from the object incident on an analyzer crystal, and obtaining an image inside the object by X-rays emitted from the analyzer crystal. The analyzer crystal is usable as both a transmission-type and reflection-type analyzer crystal, being configured to satisfy both a thickness condition that either one of X-rays along a forward diffraction direction and X-rays along a diffraction direction obtained by a dynamical diffraction action of the analyzer crystal have an intensity of nearly zero as compared to the intensity of the other with respect to the monochromatic parallel X-rays in use, and a thickness condition that the X-rays from the object satisfy a diffraction condition and are transmitted by the dynamical diffraction action of the analyzer crystal. In the case of the transmission-type analyzer crystal, either one or both of an X-ray dark-field image and an X-ray bright-field image from the transmission-type analyzer crystal are provided. In the case of the reflection-type analyzer crystal, an X-ray dark-field image transmitted through the reflection-type analyzer crystal is provided.

According to a ninth aspect the invention provides the reflection-type analyzer crystal as an asymmetric analyzer crystal.

According to a tenth aspect the present invention provides an X-ray detecting device for detecting either one or both of the X-ray dark-field image and the X-ray bright-field image and image processing equipment for creating an image by using detecting data from the X-ray detecting device.

According to an eleventh aspect the present invention provides the X-ray detecting device as a two-dimensional detector or a line sensor one-dimensional detector.

According to a twelfth aspect the present invention provides the image processing equipment capable of creating either one or both of X-ray dark-field tomography and X-ray bright-field tomography, or either one or both of X-ray dark-field stereography and X-ray bright-field stereography.

According to a thirteenth aspect the present invention provides means for monochromating and parallelizing X-rays from an X-ray source.

According to a fourteenth aspect the present invention provides the means for monochromating and parallelizing the X-rays, or a pre crystal device, as a symmetric or asymmetric monochromator.

According to a fifteenth aspect the present invention provides atomic lattice planes of the pre crystal device, or the means for monochromating and parallelizing the X-rays, and atomic lattice planes of the transmission-type analyzer crystal or reflection-type analyzer crystal parallel with each other.

The X-rays from the object are made incident on the transmission-type analyzer crystal through one or a plurality of asymmetric monochromators.

According to a sixteenth aspect the present invention provides that the X-rays from the object are made incident on the reflection-type analyzer crystal through one or a plurality of asymmetric monochromators.

According to a seventeenth aspect the present invention provides an electromagnetic wave other than the X-rays or a corpuscular beam used instead of the X-rays.

According to an eighteenth aspect the present invention provides a specific object identified by analyzing an internal structure of an object by using the nondestructive analysis method according to the already described invention, or the nondestructive analysis device according to the already described invention.

According to a nineteenth aspect the present invention provides either one or both of the X-ray dark-field image and the X-ray bright-field image obtained from the transmission-type analyzer crystal output through one or a plurality of asymmetric monochromators.

In addition, according to a twentieth aspect the invention provides the X-ray dark-field image obtained from the reflection-type analyzer crystal output through one or a plurality of asymmetric monochromators.

Figure 1:
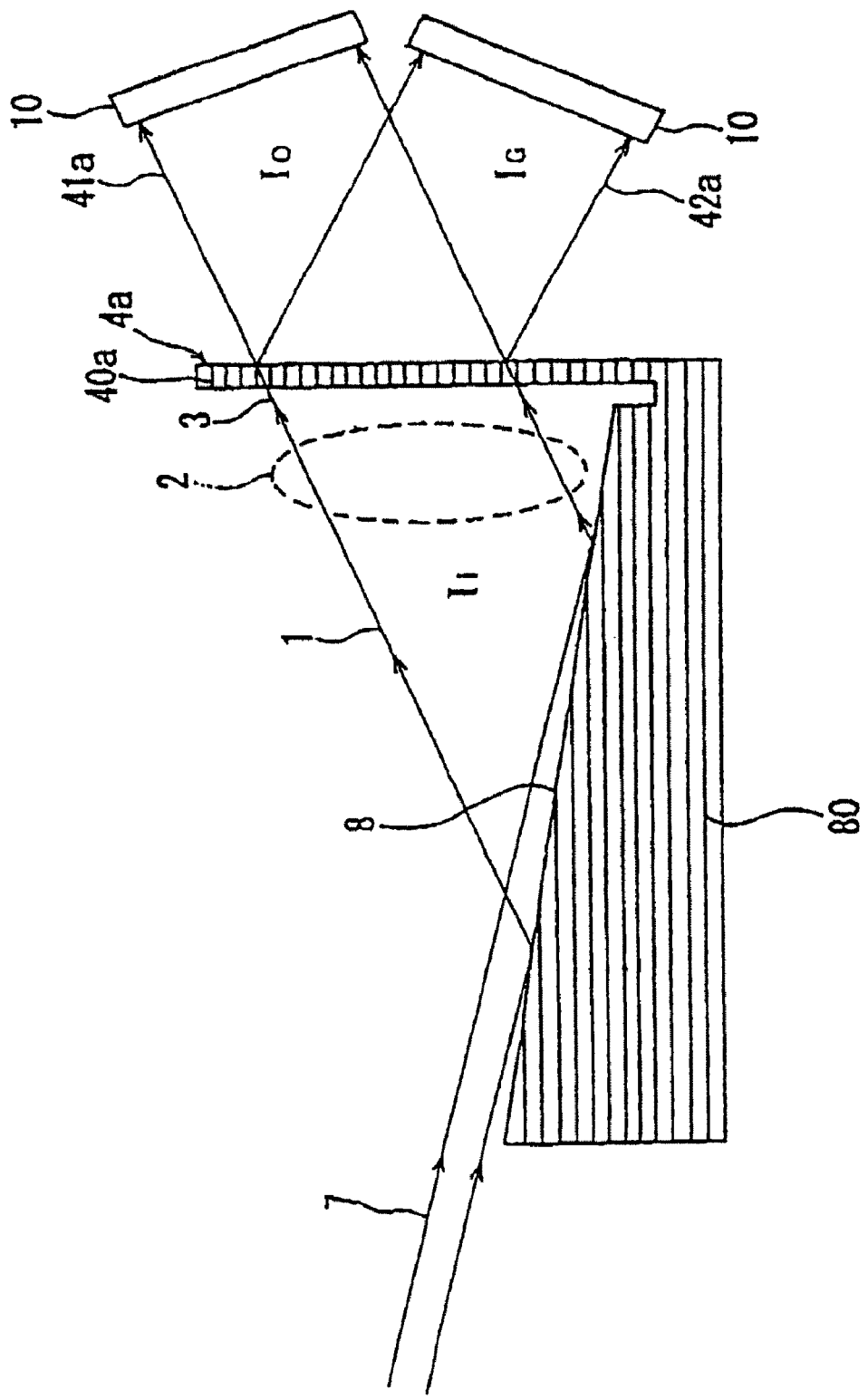
FIG. 1 is a diagram illustrating an embodiment of the invention of this application for the case of using a transmission-type analyzer crystal.

It should be noted that the reference numerals in the drawings represent the following:

1 monochromatic parallel X-rays
2 object
3 X-rays from the object
4$a$ transmission-type analyzer crystal
   40$a$ atomic lattice planes
   41$a$ X-rays along the forward diffraction direction
   42$a$ X-rays along the diffraction direction 4b reflection-type analyzer crystal; 40b atomic lattice planes
41b transmission X-rays
42b reflection X-rays
5 X-ray dark-field image
6 X-ray bright-field image
7 incident X-rays
8 asymmetric monochromator
8a, 8b, 8c, 8d asymmetric monochromators
80 atomic lattice planes
9 collimator
90 atomic lattice planes
10 X-ray detecting device
11 slit plate.

DETAILED DESCRIPTION OF THE INVENTION

First Embodiment

The invention of this application uses, for example, monochromators or asymmetric monochromators as pre crystal devices which serve as monochromatization and parallelization means. In this case, it is predicated that the monochromators or asymmetric monochromators are arranged with their atomic lattice planes in parallel with the atomic lattice planes of a transmission-type analyzer crystal (4a) or a reflection-type analyzer crystal (4b), so that an achromatic condition (the condition for simultaneous diffraction in all the wavelengths including an accompanying wavelength distribution $\Delta\lambda$ of the wavelength $\lambda$ of the monochromatic X-rays) is satisfied to reduce the angular distribution of the resulting diffraction X-rays as much as possible for increased angular sensitivity (which refers to a difference of relative magnitude of the angular distribution of X-rays obtained from the X-rays from the object with respect to the angular distribution of the monochromatic parallel X-rays in use). An important factor of the present invention lies in that the transmission-type analyzer crystal (4a) or the reflection-type analyzer crystal (4b) of fixed angle can grasp all the phenomena, such as refraction, within an object (2).

Then, when the thickness of the transmission-type analyzer crystal is set at a certain value with respect to the monochromatic parallel X-rays in use, the X-rays in the object-passing direction undergo the effect of the transmission-type analyzer crystal to result in either of the two cases: (I) in the forward direction on the one hand, the X-rays along the forward diffraction direction show an intensity of nearly zero while refraction X-rays and the like from the object are observed with some intensity, and on the other hand, diffracted direction, the X-rays along the diffraction direction are observed simultaneously with refraction X-rays and the like from the object; and (II) the X-rays along the forward diffraction direction on the one hand are observed simultaneously with refraction X-rays and the like from the object, and the X-rays along the diffraction direction on the other hand show an intensity of nearly zero while refraction X-rays and the like from the object are observed. In the case (I), an X-ray dark-field image is obtained in the transmission direction, i.e., the forward direction. An X-ray bright-field image is obtained in the diffraction direction. In the case (II), an X-ray bright-field image is obtained in the transmission direction, i.e., the forward direction. An X-ray dark-field image is obtained in the diffraction direction.

Figure 2:
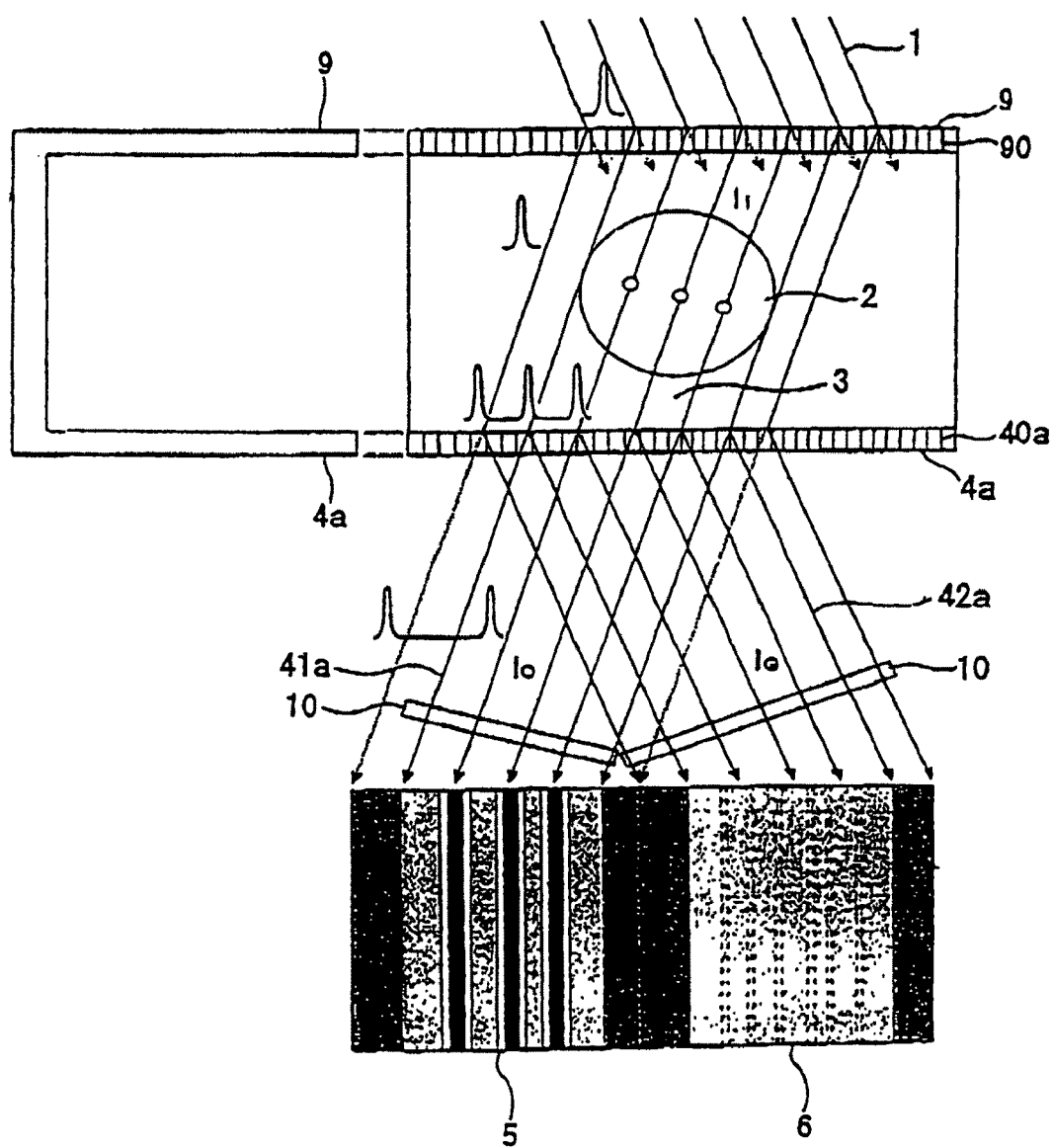
FIG. 2 is a diagram illustrating another embodiment of the invention of this application for the case of using a transmission-type analyzer crystal.

Now consider the case illustrated in FIGS. 1 and 2, for example. An object (2) to be analyzed is irradiated with monochromatic X-rays $I_i$ (1). Transmission X-rays from the object (2), and such X-rays as refraction X-rays, diffraction X-rays, or small angle scattering X-rays, and even secondary X-rays (for convenience of explanation, these will be collectively referred to as X-rays from the object) (3) are made incident on a transmission-type analyzer crystal (4a) to utilize the dynamical diffraction action of the transmission-type analyzer crystal (4a) (technically, based on the case called Laue case) at this time. The thickness of the transmission-type analyzer crystal (4a) is initially set to such a thickness that when there is no object, either ones of the X-rays (41a) along the forward diffraction direction (also referred to, equivalently, as diffraction X-rays along the incident direction or X-rays along the transmission diffraction direction) and the X-rays (42a) along the diffraction direction obtained by the dynamical diffraction action of the transmission-type analyzer crystal (4a) show an intensity of approximately zero (including exactly zero; the same holds hereinafter) as compared to the intensity of the others with respect the monochromatic parallel X-rays in use. This makes it possible to obtain either one or both of an X-ray dark-field image (5) and an X-ray bright-field image (6) of an image inside the object (2) at a time.

Figure 3:
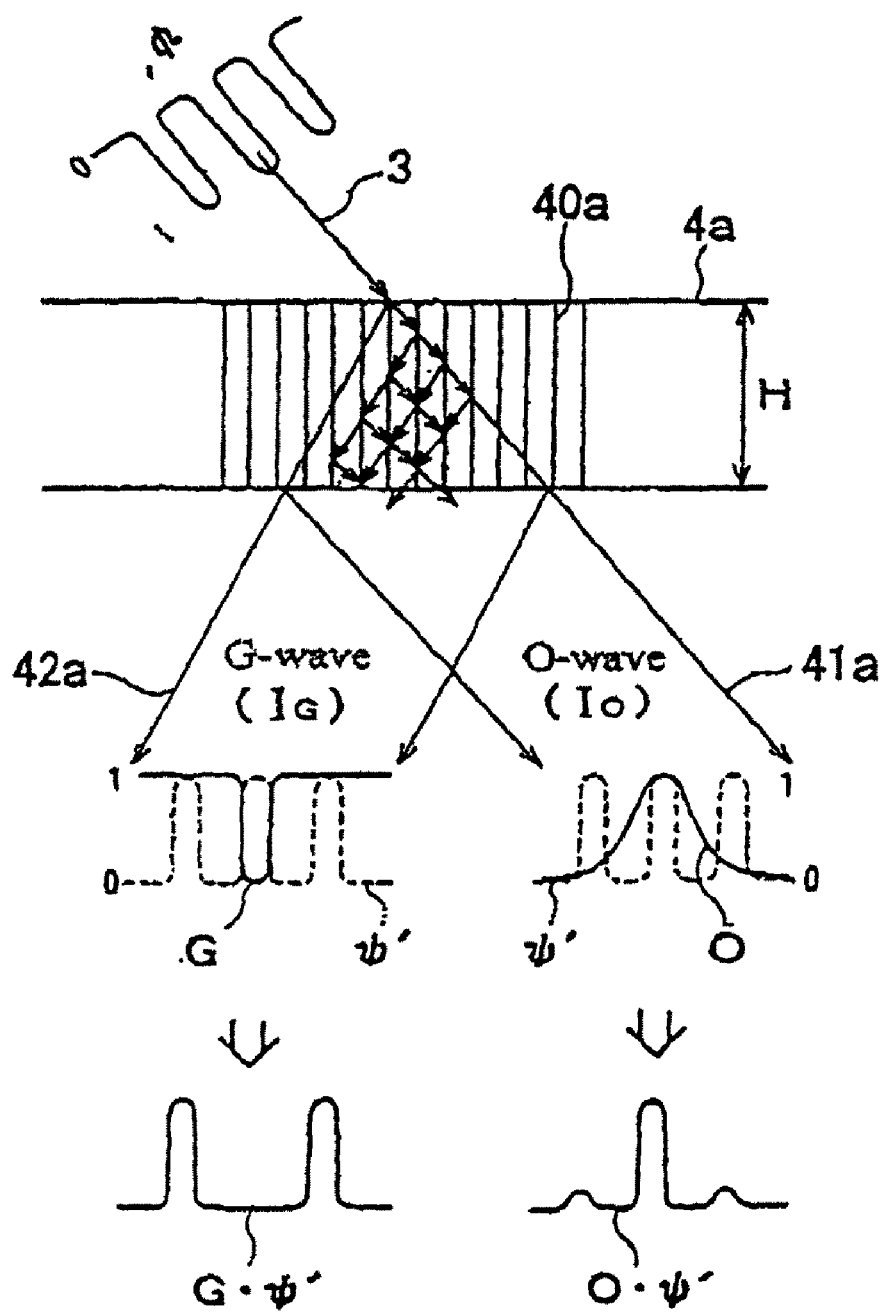
FIG. 3 is a diagram for explaining the dynamical diffraction action of the transmission-type analyzer crystal.

To be more specific, as also illustrated enlarged in FIG. 3, the dynamical diffraction action means an effect resulting from multiple scattering of X-rays in a nearly perfect crystal. The X-rays are thus output as divided into a wave (called O-wave) along the forward direction (also referred to as incident direction or transmission direction) and a wave (called G-wave) along the diffraction direction, the O-wave and the G-wave being reflected for a plurality of times repeatedly on a number of crystal lattice planes in the crystal.

Here, the relationship among the O-wave, the G-wave, and the thickness H of the transmission-type analyzer crystal (4a) can be expressed by the following equations 1:

$$I_O = \frac{W^2 + \cos^2\left(\pi H \frac{\sqrt{W^2+1}}{\Lambda}\right)}{W^2+1} I_i \quad [\text{Eq. 1}]$$

$$I_G = \frac{\sin^2\left(\pi H \frac{\sqrt{W^2+1}}{\Lambda}\right)}{W^2+1} I_i$$

$$I_O + I_G = 1$$

$I_O$: Intensity of O-wave, $I_G$: Intensity of G-wave $I_i$: Intensity of incident wave $H$: Thickness of an analyzer crystal (4)

$$W = \frac{2\Lambda \sin\theta_B}{\lambda}(\theta - \theta_B - \Delta\theta_0)$$

$\Lambda$: Extinction distance, $\lambda$: X-ray wave length $\theta_B$: The Bragg angle, $\theta$: glancing angle $$\Delta\theta_0 = \frac{2(1-n)}{\sin 2\theta_B}: \text{Bragg angle}$$

$$1 - n = -\frac{r_e \lambda^2}{2\pi V} F_0$$

$n$: Refractive index, $r_e$: Classical electron radius $V_c$: Volume of unit crystal lattice = volume of unit cell $F_0: \frac{2\sin\theta_B}{\lambda} = 0$ Crystal structure factor in case of $\frac{2\sin\theta_B}{\lambda} = 0$
(scattering along transmission direction)

$$\Lambda = \frac{\lambda \cos\theta_B}{|\chi_G|}, \quad \chi_G = -\frac{r_e \lambda^2}{\lambda V_c} F_G$$

$F_G$: The crystal structure factor in case $\theta \neq 0$;.

The equations 1 basically describe the relation of the X-ray intensity of $I_O$ for the O-wave, thickness H of a transmission-type analyzer crystal (4a) and the monochromatic parallel X-rays $I_i$(1) as well as the relation of the X-ray intensity of $I_G$ for the G-wave, the thickness H of a transmission-type analyzer crystal (4a) and the monochromatic parallel X-rays $I_i$ (1).

$$|W| \leq 1 \quad [\text{Eq. 2}]$$

Under the condition of $|W| \leq 1$, the thickness H of the transmission-type analyzer crystal (4a) should be selected so that either the X-ray intensity of $I_O$ for O-wave or the X-ray intensity of $I_G$ for G-wave will be approximately zero, in other words so that either one, as compared to the other, may receive less influence of the monochromatic parallel X-rays $I_i$ (1) in use. Here, the wave that gives approximately the zero intensity forms the dark-field image (5) and the other wave forms the bright-field image (6).

That is, the following relationship holds:

$$\begin{cases} \text{Under the condition of thickness } H_O \text{ in the case given} \\ I_O \cong 0 \text{ (where } |W| \leq 1 \text{) then gives} \rightarrow \begin{cases} I_O = \text{dark-field} \\ I_G = \text{bright-field} \end{cases} \\ \text{Under the condition of thickness } H_G \text{ in the case given} \\ I_G \cong 0 \text{ (where } |W| \leq 1 \text{) then gives} \rightarrow \begin{cases} I_O = \text{bright-field} \\ I_G = \text{dark-field} \end{cases} \end{cases} \quad [\text{Eq. 3}]$$

Figure 4:
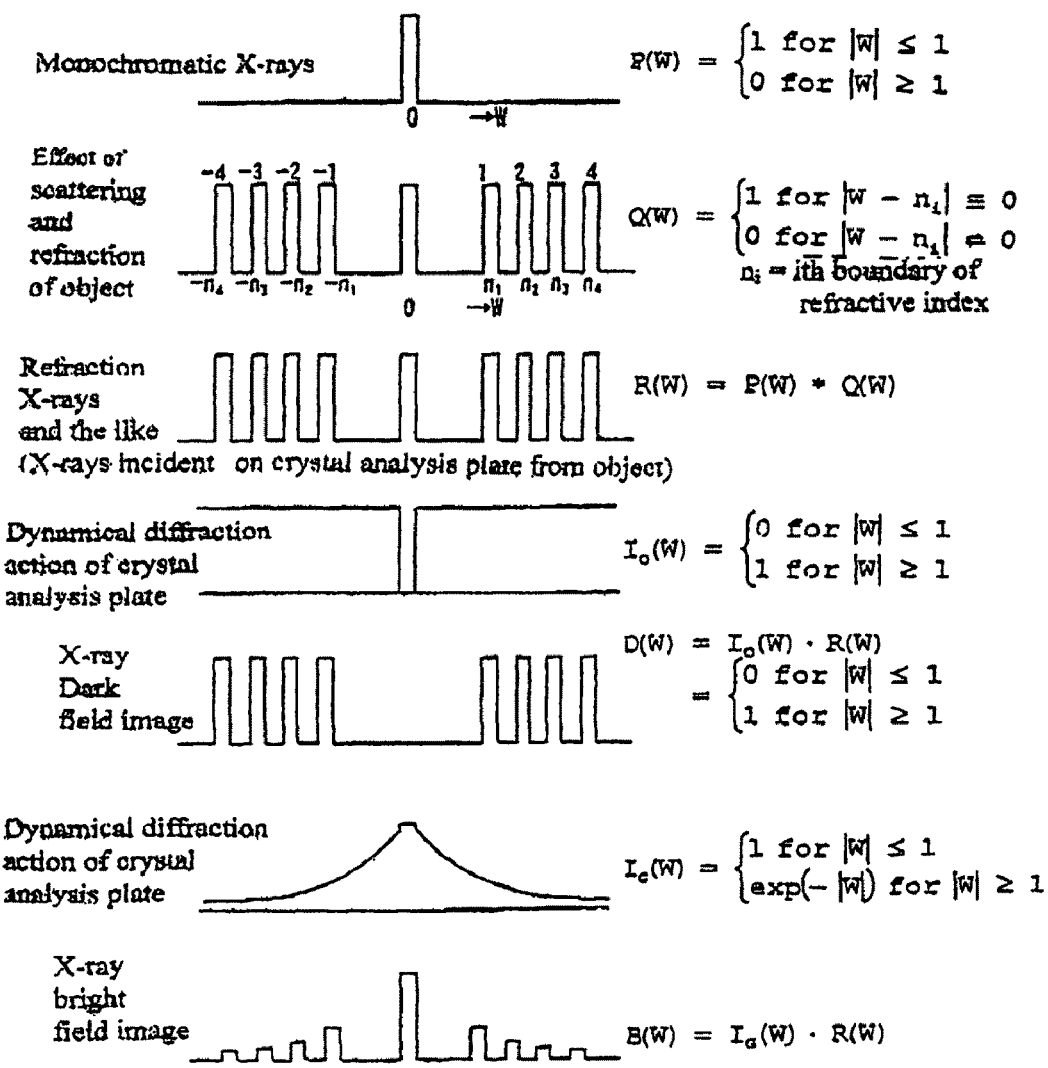
FIG. 4 is a diagram for explaining an X-ray bright-field image and an X-ray dark-field image of the transmission-type analyzer crystal.

Further description will be given of the achievement of X-ray dark-field and bright-field images by the O-wave and G-wave of the X-rays according to this selection of thickness H, with reference to FIG. 4. Initially, when the object (2) is irradiated with monochromatic parallel X-rays P(W) (1), this generates transmission X-rays, and the scattered/refracted refraction X-rays and the like R(W) (3) from the object (2), including refraction X-rays, diffraction X-rays, or small angle scattering X-rays, and even secondary X-rays, under the effects of scattering, refraction, and the like Q(W) from the elements, structures, densities, and the like of the substances of the object (2).

The atomic lattice planes of the monochromators, asymmetric monochromators, or the like serving as the means of a pre-crystal device for generating the monochromatic parallel X-rays P(W) (1) and the atomic lattice planes of the analyzer crystal are parallelized to utilize the angular-analysis capability of the analyzer crystal. In the meantime, the achromatic condition (the condition for simultaneous diffraction in all the wavelengths including the accompanying wavelength distribution Δλ of the wavelength λ of the monochromatic X-rays) is satisfied. Undergoing the effects of scattering, refraction, and the like Q(W) from the object (2), the X-rays R(W) (3) from the object (2) cause angularly distributed X-rays with respect to the generally uniform angular direction of the monochromatic parallel X-rays (1) which cause diffraction X-rays of minimum angular distribution.

When the X-rays R(W) (3) from this object (2) are incident on the transmission-type analyzer crystal (4a) at a glancing angle of θ which is formed between the monochromatic parallel X-rays (1) satisfying the equations 1 and the crystal lattice planes of the transmission-type analyzer crystal (4a), they are divided into the O-wave along the forward direction and the G-wave along the diffraction direction under the dynamical diffraction actions $I_O$(W) and $I_G$(W) of the transmission-type analyzer crystal (4a).

With respect to the angular distribution of the monochromatic parallel X-rays used in this scheme, an X-ray dark-field image is obtained as the angular difference of relative magnitude between the larger angular distribution of X-rays obtained from the object and the above X-rays.

Figure 5:
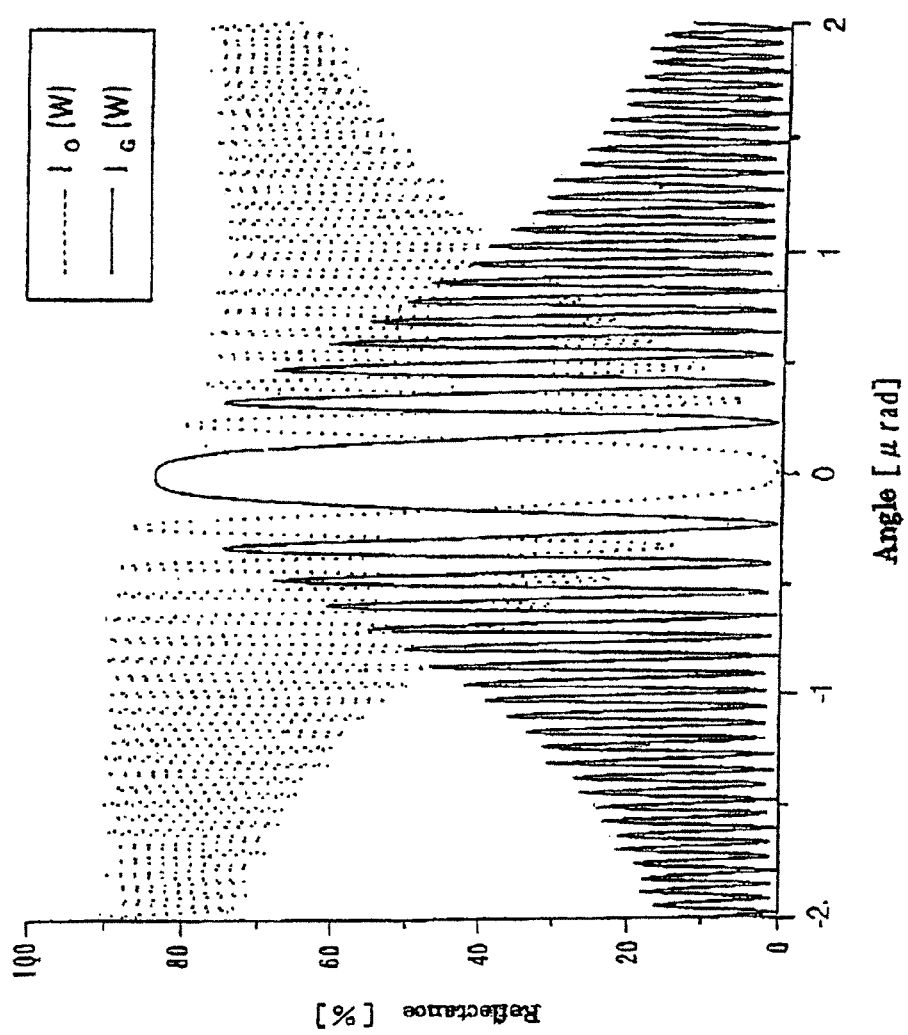
FIG. 5 is a chart illustrating a theoretical curve of the dynamical diffraction action of the transmission-type analyzer crystal.

FIG. 5 illustrates the theoretical curves of the dynamical diffraction actions $I_O$(W) and $I_G$(W) in more detail. Here, if the thickness of the transmission-type analyzer crystal (4a) is rendered so that the thickness H of the transmission-type analyzer crystal (4a) is set at $H_O$ when the intensity of the O-wave of the X-rays $I_O$=0 as shown in the foregoing equation 3, the O-wave of the X-rays constructs an X-ray dark-field image (5) under the dynamical diffraction action $I_O$(W), and the G-wave of the X-rays constructs an X-ray bright-field image (6) under the dynamical diffraction action $I_G$(W). In contrast, if the thickness H of the transmission-type analyzer crystal (4a) is set at HG when the intensity of the G-waves of the X-rays $I_G$=0 the G-wave constructs an X-ray dark-field image (5) under the dynamical diffraction action $I_G$(W), and the O-wave constructs an X-ray bright-field image (6) under the dynamical diffraction action $I_O$(W).

What is of importance here is that the intensity of the O-wave of the X-rays $I_O$ and the intensity of the G-wave of the X-rays $I_G$, satisfying the foregoing relationship, appear in certain periods with respect to the thickness H of the transmission-type analyzer crystal (4a).

Figure 6:
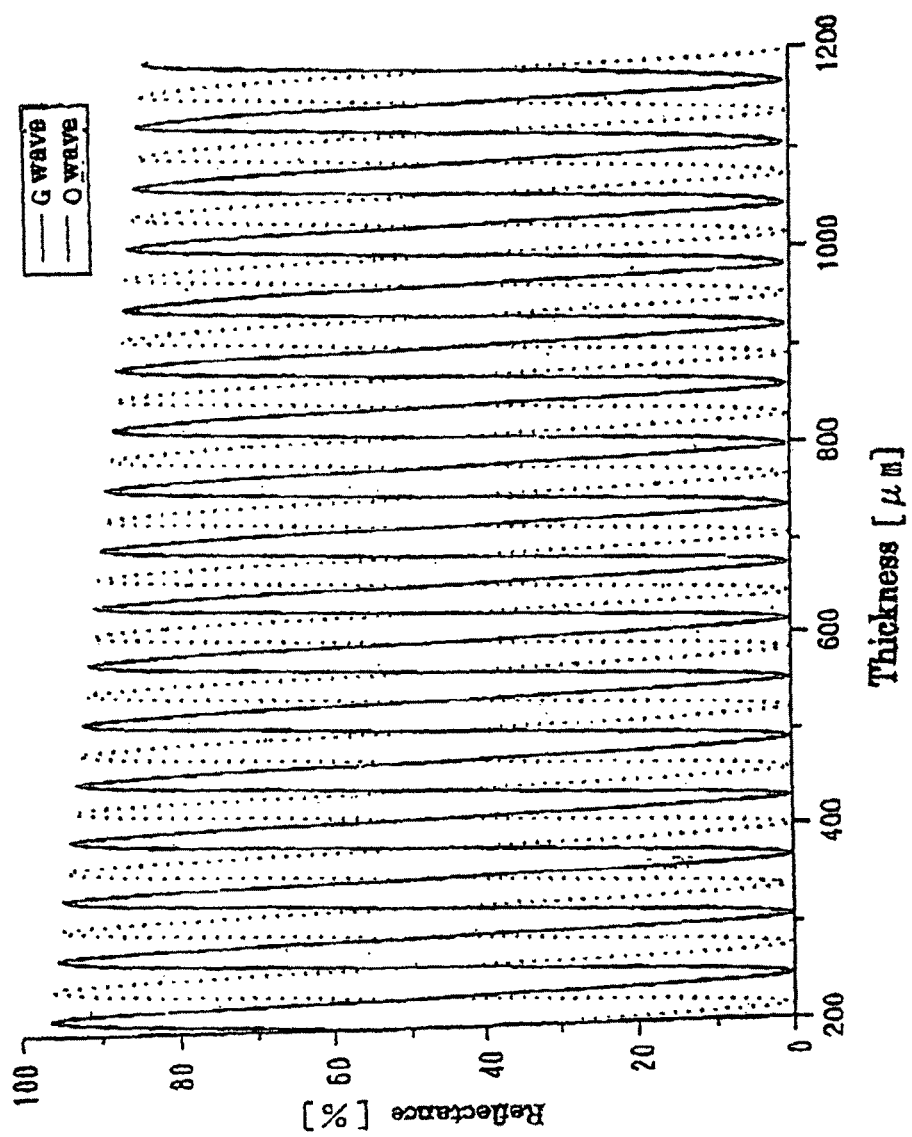
FIG. 6 is a chart illustrating the relationship between the thickness of the transmission-type analyzer crystal and an O-wave and a G-wave.

For example, when the transmission-type analyzer crystal (4a) made of a diamond-type silicon analyzer crystal having a size of crystal lattice of 5.4311 angstroms and silicon 4,4,0 reflection is used, the thicknesses H of the transmission-type analyzer crystal (4a) at which $I_O$ or $I_G$ falls to nearly zero with respect to X-rays of 35 kev in energy appear in periods of 67.5 μm as illustrated in FIG. 6. Here, $I_O$=0 when $I_G$ peaks, and $I_O$ peaks when $I_G$=0. Consequently, when the thickness of the transmission-type analyzer crystal (4a) is adjusted to this period, it is possible to obtain a high-contrast image of the object (2), in either one or both of an X-ray dark-field image (5) and an X-ray bright-field image (6), at a time without rotating the transmission-type analyzer crystal (4a) as in the conventional art. It is also shown that the thickness H of the transmission-type analyzer crystal (4a) can be changed to switch the roles.

Figure 7:
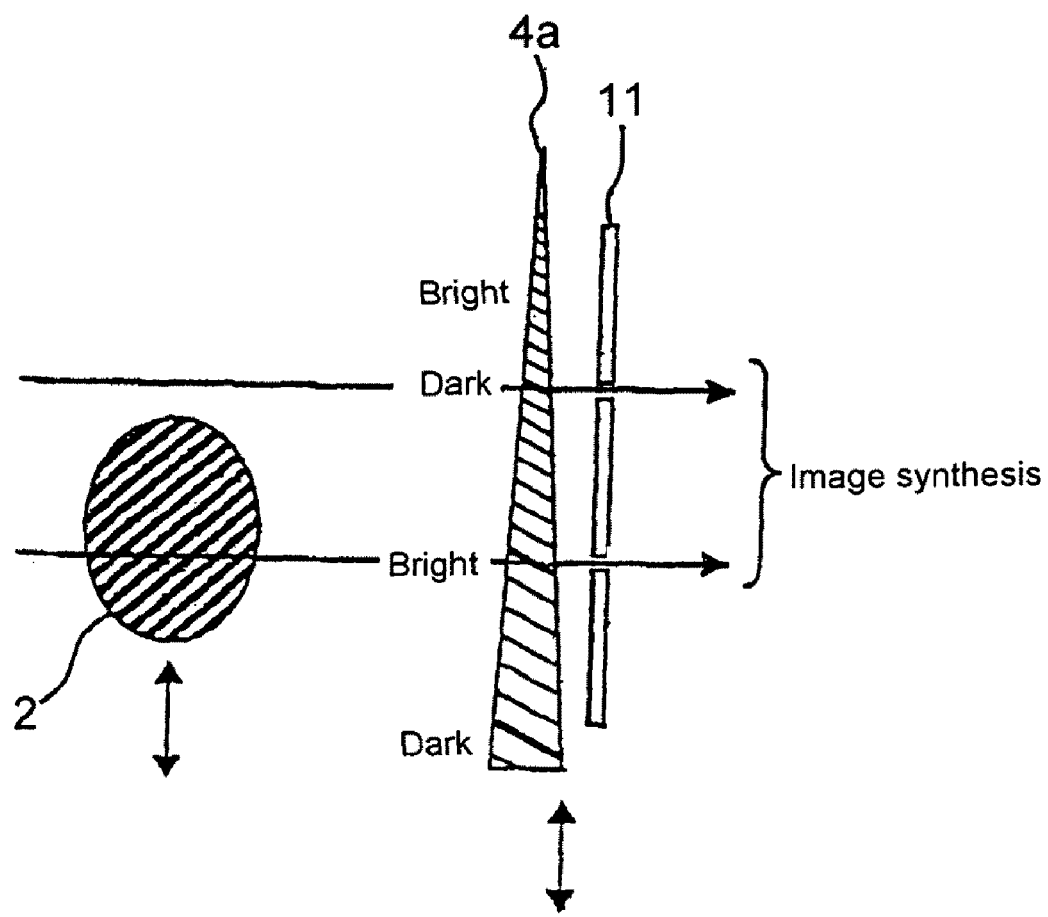
FIG. 7 is a diagram illustrating a further embodiment of the invention of this application for the case of using a transmission-type analyzer crystal.

Moreover, with consideration given to the periodicity, for example, the transmission-type analyzer crystal (4a) may be formed in a wedge shape or the like that exhibits the foregoing thicknesses periodically, in which case X-ray dark-field images (5) and X-ray bright-field images (6) are obtained in a slit fashion successively as shown in FIG. 6. Consequently, as illustrated in FIG. 7, for example, a slit plate (11) is arranged on the output side of the transmission-type analyzer crystal (4a) so that this slit plate (11) and the wedge shape transmission-type analyzer crystal (4a) can be slid and moved relative to the object (2), or conversely the object (2) can be slid and moved relative to the slit plate (11) and the wedge shape transmission-type analyzer crystal (4a), to obtain a plurality of slit-like images through the slit plate (11). Those images can be synthesized into an image or images of any fields of view, or equivalently, either one or both of an X-ray dark-field image and an X-ray bright-field image.

Here, in the X-ray dark-field image (5), either the O-wave of the X-rays of the transmission-type analyzer crystal (4a), i.e. the X-rays (41a) along the forward diffraction direction, or the G-wave of the X-rays, i.e. the X-rays (42a) along the diffraction direction, shows an intensity of nearly zero as compared to the intensity of the other with respect to monochromatic parallel X-rays (1)—in use. As is also evident from the foregoing description, this means that the unnecessary monochromatic parallel X-rays (1) affected by the intensity of the monochromatic parallel X-rays (1) are not superimposed on the X-rays R(W) (3) from the object (2), and the intensity of the unnecessary, high-intensity monochromatic parallel X-rays (1) which form an illuminated image background becomes nearly zero, or equivalently, the theoretical intensity in the absence of the object (2) becomes nearly zero.

The theoretical intensity of nearly zero is ascribable to the fact that in the absence of the object (2), there will not occur any of the X-rays R(W) (3) from the object (2), such as refraction X-rays, diffraction X-rays, small angle scattering X-rays, and the like, since there is no effect of scattering or refraction Q(W) at least from the object (2).

Meanwhile, in the X-ray bright-field image (6), either the O-wave of the X-rays, i.e. the X-rays (41*a*) along the forward diffraction direction, or the G-wave of the X-rays, i.e. the X-rays (42*a*) along the diffraction direction, has an intensity of the X-rays under the effect of the monochromatic parallel X-rays (1) as compared to the intensity of the others. As is also evident from the foregoing description, this means that the unnecessary monochromatic parallel X-rays (1) affected by the intensity of the monochromatic parallel X-rays (1) are superimposed on the X-rays R(W) (3) from the object (2) and have the intensity of the unnecessary, high-intensity monochromatic parallel X-rays (1) which form an illuminated image background, or equivalently, the theoretical intensity in the absence of the object (2) generally coincides with that of the monochromatic parallel X-rays (1).

The transmission-type analyzer crystal (4*a*) capable of such intensity settings may have thicknesses in the range of, e.g., several micrometers to several tens of millimeters. The range varies, as can be seen from the foregoing equations 1, with various factors including the size of the crystal lattice, and the intensities and wavelengths of the X-rays, X-rays (3) incident from the object (2). Moreover, in practical terms, it is desirable that the transmission-type analyzer crystal (4*a*) in this case have a required finishing precision of 1% or less of the thickness.

The X-rays (41*a*) along the forward diffraction direction and the X-rays (42*a*) along the diffraction direction from the transmission-type analyzer crystal (4*a*) given the foregoing thickness setting, are detected by the X-ray detecting devices (10) (see FIGS. 1 and 2). Images are created by image processing equipment (not shown, but configured to be capable of receiving the detecting data of X-rays) by using the detecting data of X-rays from the X-ray detecting devices (10).

In the example of FIG. 2, the X-ray dark-field image (5) is created from $I_O$, and the X-ray bright-field image (6) from $I_G$.

Second Embodiment

Now, in the case of a reflection-type analyzer crystal, it is publicly known that an X-ray bright-field image is obtained since monochromatic parallel X-rays passing through an object without causing reaction with the object are reflected by the reflection-type analyzer crystal on the one hand while X-rays from the object are observed at the same time. The present invention consists in that an X-ray dark-field image is obtained for situations where monochromatic parallel X-rays passing through an object without causing reaction with the object are reflected, not transmitted, by the reflection-type analyzer crystal on the one hand while X-rays from the object are transmitted by the reflection-type analyzer crystal in the transmission direction and observed on the other hand.

Figure 8:
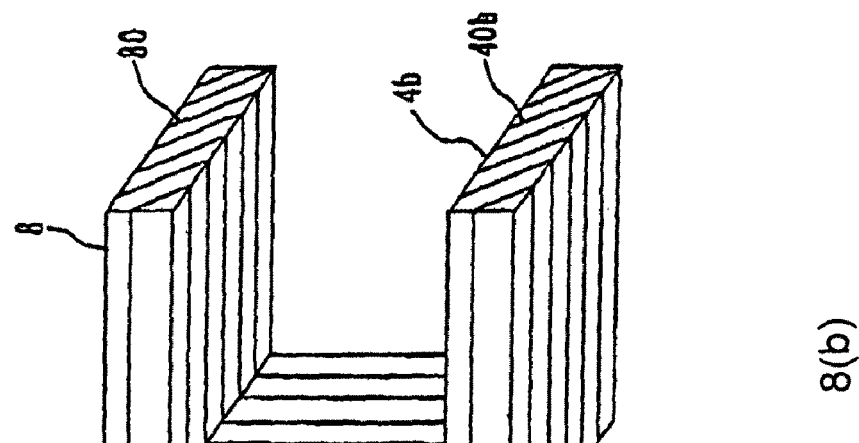
FIG. 8($a$) is a diagram illustrating an embodiment of the invention of this application for the case of using a reflection-type analyzer crystal, and FIG. 8($b$) is a perspective view illustrating the reflection-type analyzer crystal.
Figure 8:
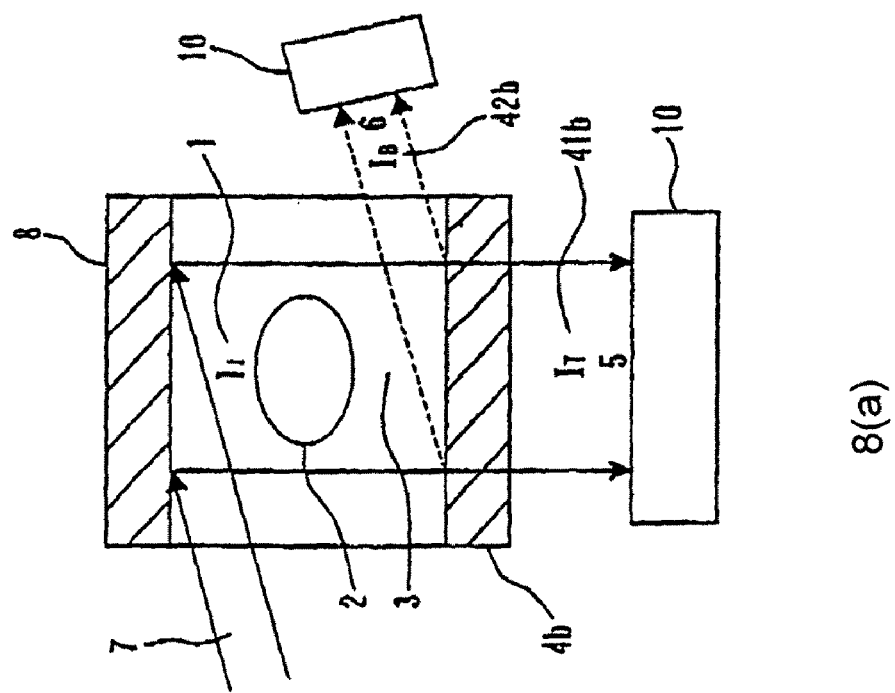

For example, as illustrated in FIGS. 8(*a*), 8(*b*), and 9, when a reflection-type analyzer crystal (4*b*) is used, an object (2) to be analyzed is irradiated with monochromatic parallel X-rays $I_i$ (1) via an asymmetric monochromator (8). Refraction X-rays and the like (3) from the object (2) are made incident on the reflection-type analyzer crystal (4*b*), at which time the dynamical diffraction action (technically based on a case called the Bragg case) of the reflection-type analyzer crystal (4*b*) is utilized so that in the reflection-type analyzer crystal (4*b*), the X-rays (3) from the object (2) satisfy the diffraction condition and are transmitted by the dynamical diffraction action of the reflection-type analyzer crystal (4*b*).

To be more specific, when the object (2) is initially irradiated with the monochromatic parallel X-rays (1), X-rays R(W) (3) occur from the object (2) under the effect of scattering, refraction, and the like Q(W) from the object (2). The atomic lattice planes of the monochromators, asymmetric monochromators (8) or the like serving as the means of a pre crystal device for generating the monochromatic parallel X-rays (1), and the atomic lattice planes of the analyzer crystal are parallelized to utilize the angular-analysis capability of the analyzer crystal. In the meantime, the achromatic condition (the condition for simultaneous diffraction in all the wavelengths including an accompanying wavelength distribution $\Delta\lambda$ of the wavelength $\lambda$ of the monochromatic X-rays) is satisfied. Undergoing the effects of scattering, refraction, and the like Q(W) from the object (2), the X-rays R(W) (3) from the object (2) cause angularly distributed X-rays with respect to the generally uniform angular direction of the monochromatic parallel X-rays (1) which cause diffraction X-rays of minimum angular distribution. When the X-rays R(W) (3) from this object (2) are incident on the reflection-type analyzer crystal (4*b*) at an angle of $\theta$ which is formed between the monochromatic parallel X-rays (1) and the crystal lattice planes of the reflection-type analyzer crystal (4*b*), the monochromatic parallel X-rays (1) are reflected under the dynamical diffraction action of the reflection-type analyzer crystal (4*b*).

With respect to the angular distribution of the monochromatic parallel X-rays (1) used in this scheme, in the transmission direction, an X-ray dark-field image is obtained as the angular difference of relative magnitude between the larger angular distribution of X-rays R(W) (3) obtained from the object (2) and the above X-rays (1).

Consequently, while the atomic lattice planes of the monochromators which generate the monochromatic parallel X-rays and the atomic lattice planes of the analyzer crystal are parallelized to utilize the angular-analysis capability of the analyzer crystal, it is the effect of multiple scattering and refraction of X-rays in a nearly perfect crystal as is also illustrated enlarged in FIG. 3.

The X-rays are thereby reflected individually on a number of crystal lattice planes in the crystal for a number of times repeatedly. In the case of the reflection-type analyzer crystal (4*b*), the X-rays are almost totally reflected in the uniform angular direction of the monochromatic parallel X-rays (1) according to the principle of Bragg reflection. Under the effect of scattering and refraction Q(W) from the elements, structures, densities, and the like of the substances of the object (2), the transmission X-rays and the X-rays R(W) (3) from the object (2), including refraction X-rays, diffraction X-rays, or small angle scattering X-rays, and even secondary X-rays, cause angularly distributed X-rays. Thus, the X-rays R(W) (3) from this object (2) also emerge in the transmission direction.

That is, in the X-ray dark-field image (5), the monochromatic parallel X-rays (1) are Bragg-reflected by the crystal structure of the reflection-type analyzer crystal (4*b*), and the X-rays R(W) (3) from the object (2) are transmitted to become nearly zero in terms of the intensity of the monochromatic parallel X-rays (1).

This means that the unnecessary monochromatic parallel X-rays (1) affected by the intensity of the monochromatic parallel X-rays (1) are not superimposed on the X-rays R(W) (3) from the object (2), and the intensity of the unnecessary, high-intensity monochromatic parallel X-rays (1) which form an illuminated image background become nearly zero, or equivalently, the theoretical intensity in the absence of the object (2) becomes nearly zero.

In this case, the angle between the monochromatic parallel X-rays (1) and the reflection-type analyzer crystal (4b) and the thickness of the reflection-type analyzer crystal (4b) are also given settings at which a preferable contrast is obtained in terms of an intensity ratio between the reduced intensity of the monochromatic parallel X-rays (1) after the Bragg reflection and the intensity of the X-rays R(W) (3), or transmission X-rays $I_T$ (41b). This makes it possible to obtain the X-ray dark-field image (5) that is created from the transmission X-rays $I_T$ (41b) from the reflection-type analyzer crystal (4b).

In this case, the angle between the monochromatic parallel X-rays (1) and the reflection-type analyzer crystal (4b) may also be given another setting to satisfy the diffraction condition by the dynamical diffraction action of the reflection-type analyzer crystal (4b), so as to obtain an X-ray bright-field image (6) that is created by reflection X-rays $I_B$ (42b) according to the Bragg reflection condition. That is, in the X-ray bright-field image (6), the monochromatic parallel X-rays (1) in use and the X-rays R(W) (3) from the object (2) are both reflected to have the intensity of the X-rays under the effect of the monochromatic parallel X-rays (1). The unnecessary monochromatic parallel X-rays (1) affected by the intensity of the monochromatic parallel X-rays (1) are superimposed with the X-rays R(W) (3) to have even the intensity of the unnecessary, high-intensity monochromatic parallel X-rays (1) which form an illuminated image background.

Now, to eliminate and reduce the unnecessary monochromatic parallel X-rays (1) that are incident on the reflection-type analyzer crystal (4b) and superimposed with the X-ray dark-field image (5), i.e., the monochromatic parallel X-rays (1) that form the unnecessary illuminated background in the X-ray dark-field image (5) in particular, the monochromatic parallel X-rays (1) are Bragg-reflected, or equivalently, reduced by Bragg reflection through the stages of a number of respective lattice planes in the crystal structure of the reflection-type analyzer crystal (4b) at a certain incident angle or smaller with respect to the crystal structure of the reflection-type analyzer crystal (4b).

Figure 9:
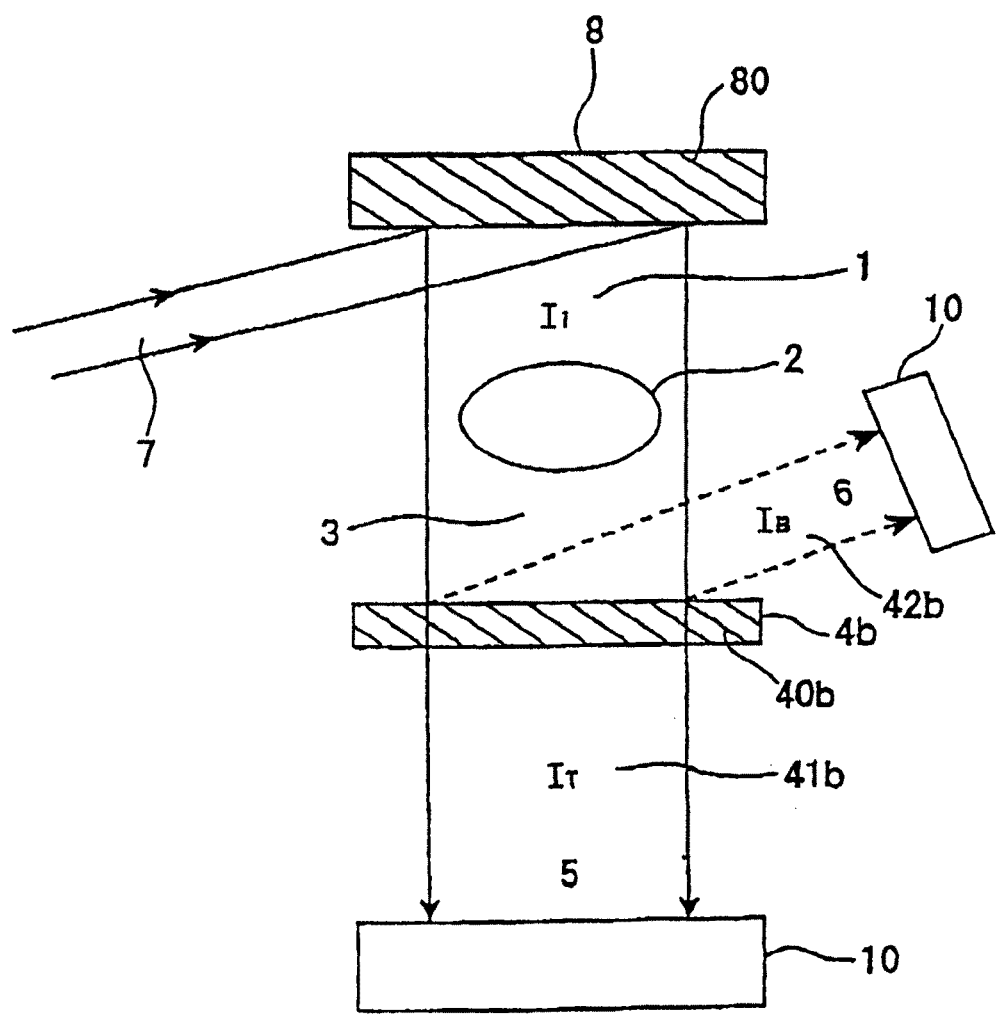
FIG. 9 is a diagram illustrating another embodiment of the invention of this application for the case of using a reflection-type analyzer crystal.

Furthermore, through the use of the asymmetric reflection-type analyzer crystal (4b) shown in FIGS. 8 and 9, such X-rays are sufficiently reflected for reduction.

The reflection-type analyzer crystal (4b) can thus be made thinner so that the X-rays R(W) (3) from the object (2) are transmitted to obtain an X-ray dark-field image of favorable contrast.

That is, the present invention provides technology for enhancing and obtaining a small amount of X-rays R(W) (3) from the object (2) in the transmission direction of the reflection-type analyzer crystal (4b), and reducing the monochromatic parallel X-rays having a high intensity, thereby improving so-called signal-to-noise ratio.

Third Embodiment

X-Ray Detecting Device

In the first embodiment and second embodiment described above, the X-rays from the transmission-type analyzer crystal (4a) or the reflection-type analyzer crystal (4b) are detected by the X-ray detecting devices (10). These X-ray detecting devices (10) may be flat-type panels, columnar panels, or the like based on two-dimensional detectors (such as an X-ray film, a nuclear plate, an X-ray image pick-up tube, an X-ray fluorescence multiplier tube, an X-ray image intensifier, an X-ray imaging plate, an X-ray CCD, and an X-ray imaging detector by amorphous element), or line sensor one-dimensional detectors.

Which X-ray detecting devices (10) to use may be selected arbitrarily depending on the type, condition, and the like of the object (2) to be analyzed. In addition, combination scanning of, for example, object movement, rotation, tilt, etc., with the line sensor one-dimensional detectors or two-dimensional detectors is useful for the creation of tomography and stereography by image processing equipment to be described later. For example, X-ray computed tomography technology can be introduced to obtain new nondestructive analysis images.

<Image Processing Equipment>

The image processing equipment (not shown) is capable of creating ordinary X-ray scattering images as either one or both of the X-ray dark-field image (5) and the X-ray bright-field image (6), based on the detecting data of X-rays from the X-ray detecting devices (10) described above. The image processing equipment may have the capability of creating X-ray dark-field and bright-field tomography and stereography through image synthesis processing or the like.

<X-Ray Source>

An X-ray source (not shown) of the X-rays for the object (2) to be irradiated with may also be selected arbitrarily according to the object (2) to be analyzed. For example, one capable of generating X-rays having a wavelength=approximately 0.5 angstroms or shorter, an effective focal spot=approximately 0.5 mm×0.5 mm or smaller, and an output=approximately 50 W or higher may be used for industrial material. For medical applications, one capable of generating X-rays having a wavelength=approximately 0.3 angstroms or shorter, an effective focal spot=approximately 0.5 mm×0.5 mm or smaller, and an output=approximately 1000 W or higher (pulses available) may be used.

<Monochromatization and Parallelization Means>

The X-rays from the X-ray source described above must reach the object (2) in the form of a monochromatic beam as well as a parallel beam (also referred to as a plane wave).

This monochromatization and parallelization can be effected, for example, by using a parabolic mirror made of a multiple layer mirror. Alternatively, a parallel beam may be created through condensation by a parabolic reflection mirror or capillary, followed by monochromatization by monochromators or asymmetric monochromators.

In the example of FIG. 1, the incident X-rays (7) from the X-ray source (not shown) are monochromated and parallelized by the asymmetric monochromator (8).

In the example of FIG. 2, the direction of the monochromatic parallel X-rays (1) from the asymmetric monochromator (8) (not shown) is changed by the collimator (9) for irradiation of the object (2).

This collimator (9) itself may also be used as a monochromator for monochromatization and parallelization. Naturally, the means for monochromatization and parallelization are not limited thereto. Various means publicly known heretofore may be used as appropriate. These means for monochromatization and parallelization will be referred to collectively as pre-crystal devices.

Now, when the monochromator or the asymmetric monochromator (8) is used as the monochromatization and parallelization means, it is of extreme importance that the monochromator or the asymmetric monochromator (8) is arranged with its atomic lattice planes (80) in parallel with the atomic lattice planes (40a), (40b) of the transmission-type analyzer crystal (4a) or the reflection-type analyzer crystal (4b) as shown in FIGS. 1, 2, 8, and 9 (in FIG. 2, the atomic lattice planes (90) of the collimator (9) are also arranged in parallel).

This satisfies the achromatic condition and reduces the angular distribution of the resulting diffraction X-rays as much as possible, with an increase in angular sensitivity. It therefore becomes possible to grasp all the phenomena within the object (2), such as refraction, by the transmission-type analyzer crystal (4a) or the reflection-type analyzer crystal (4b) of a fixed angle.

Incidentally, FIG. 1 shows the asymmetric monochromator (8) and the transmission-type analyzer (4a) which are integrated with each other, FIG. 2 shows the collimator (9) and the transmission-type analyzer crystal (4a) which are unified with each other into a channel-cut shape, and FIG. 8 shows the asymmetric monochromator (8) and the reflection-type analyzer crystal (4b) which are unified with each other into a channel-cut shape. It will be appreciated that the two may be separated or coupled loosely. FIG. 9 shows an example where the asymmetric monochromator (8) and the reflection-type analyzer crystal (4b) are arranged separately.

In any case, the asymmetric monochromator (8), the collimator (9), and the transmission-type analyzer crystal (4a) or the reflection-type analyzer crystal (4b) must be assembled and adjusted so that their atomic lattice planes (80), (90), (40a), (40b) are in parallel with each other.

<Enlarged Image Acquisition Means>

Figure 10:
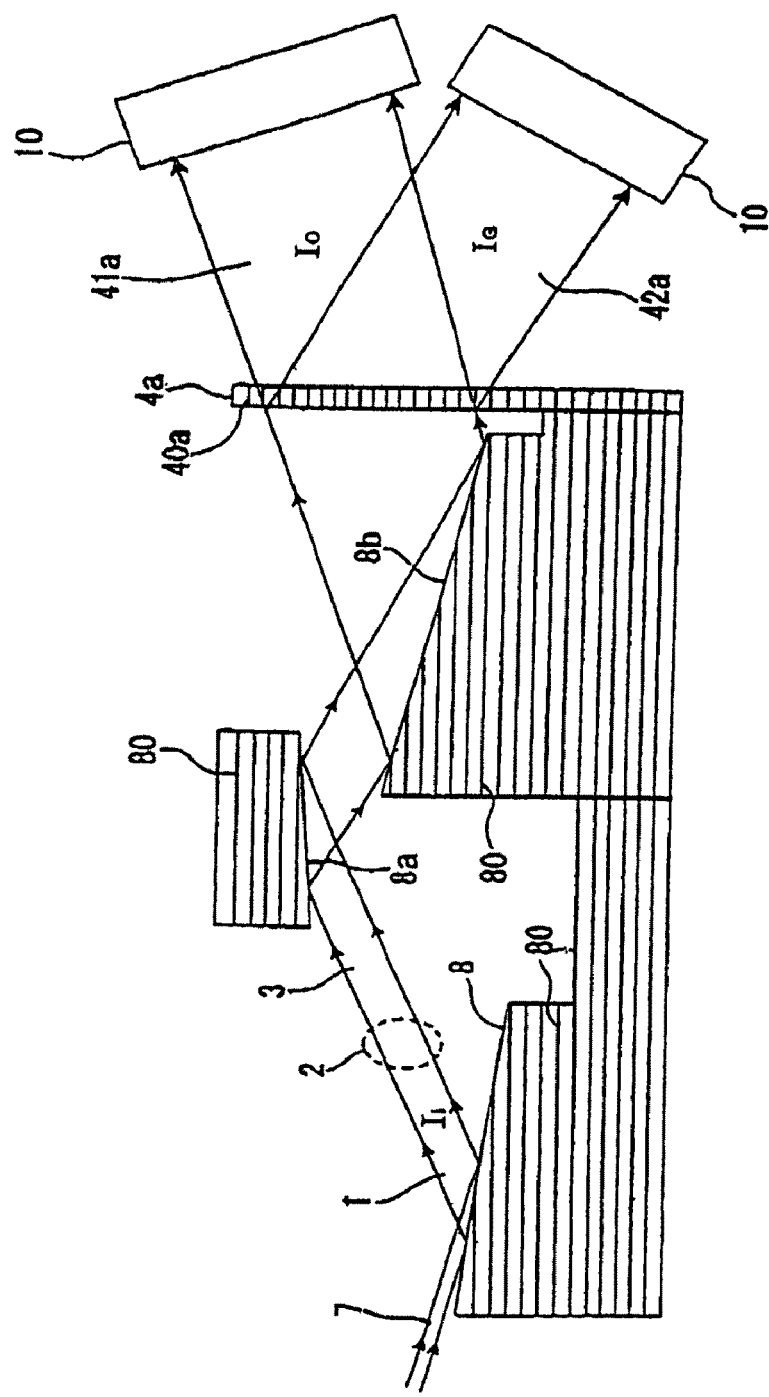
FIG. 10 is a diagram illustrating an embodiment of the invention of this application for situations where asymmetric monochromators are interposed between an object and a transmission-type analyzer crystal.

When enlarged images of the X-rays from the transmission-type analyzer crystal (4a) or the reflection-type analyzer crystal (4b) are desired, the incident X-rays (7) from the X-ray source (not shown) are monochromated and parallelized by the asymmetric monochromator (8), the object (2) is irradiated with the monochromatic parallel X-rays (1), and the X-rays (3) from the object (2) are further passed through one or a plurality of composite asymmetric monochromators (8a), (8b) before incidence on the transmission-type analyzer crystal (4a), as illustrated in FIG. 10, for example. This makes it possible to obtain the X-ray dark-field image (5) and the X-ray bright-field image (6) created by the X-rays (41a) along the forward diffraction direction and the X-rays (42a) along the diffraction direction from the transmission-type analyzer crystal (4a) as enlarged images, and to obtain them as images of higher resolution.

Figure 11:
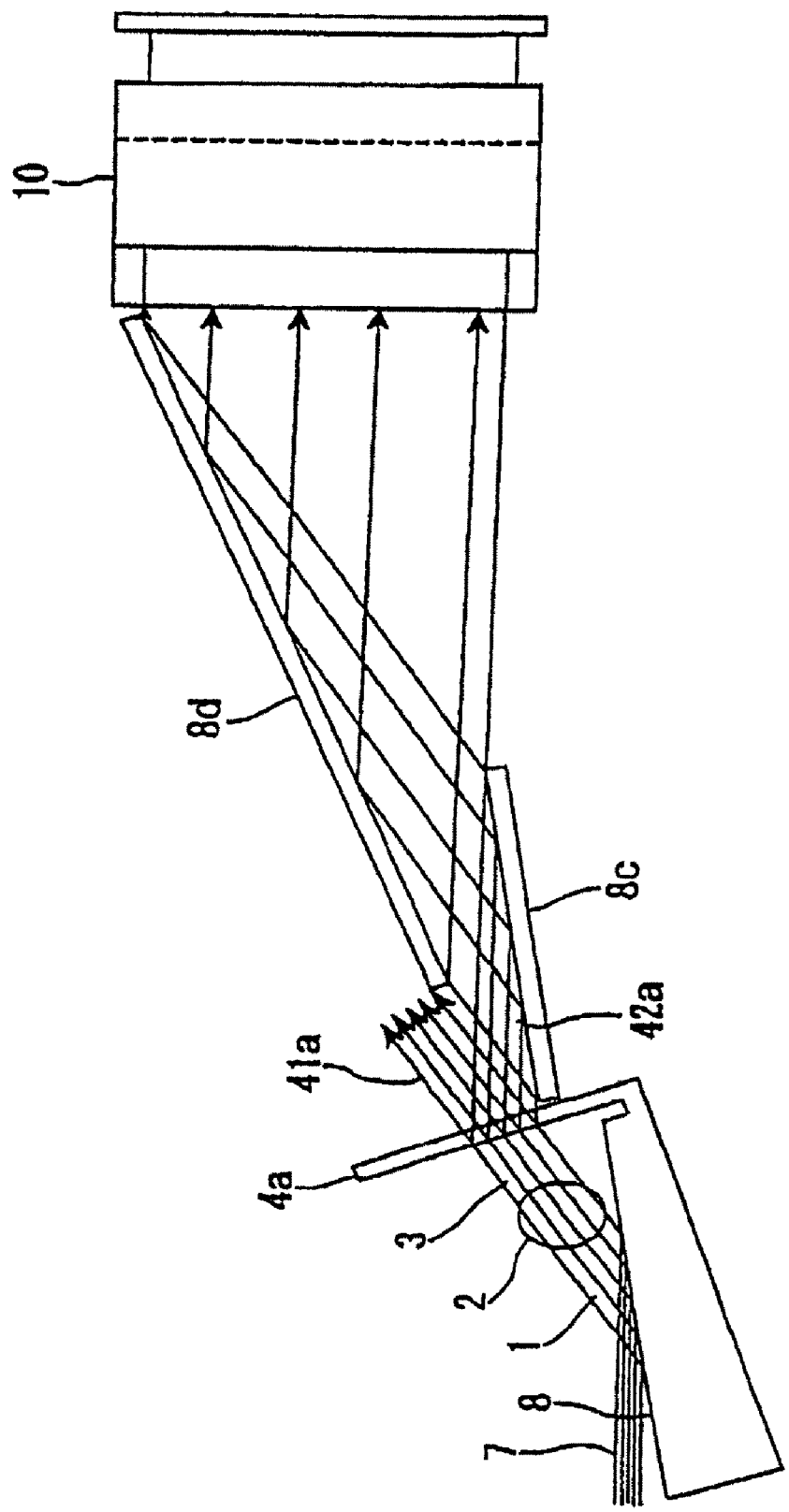
FIG. 11 is a diagram illustrating an embodiment of the invention of this application for situations where asymmetric monochromators are interposed between a transmission-type analyzer crystal and an X-ray detecting device.

Moreover, as illustrated in FIG. 11, for example, the X-rays (41a) along the forward diffraction direction and the X-rays (42a) along the diffraction direction from the transmission-type analyzer crystal (4a) may be further passed through one or a plurality of composite asymmetric monochromators (8c), (8d) before being output to the X-ray detecting devices (10). This also makes it possible to obtain the X-ray dark-field image (5) and the X-ray bright-field image (6) as enlarged images.

It should be noted that while FIGS. 10 and 11 show embodiments for the case of using the transmission-type analyzer crystal (4a), the reflection-type analyzer crystal (4b) can also be used to obtain enlarged images and high resolution images, with such a configuration that one or a plurality of composite asymmetric monochromators (8a), (8b), (8c), (8d) are arranged before and behind the reflection-type analyzer crystal (4b).

Moreover, as in FIG. 1, the asymmetric monochromators (8), (8b) and the transmission-type analyzer crystal (4a) are also integrated with each other in FIG. 10 (those of FIG. 11 are substantially the same as in FIG. 1).

The two parts may be separated or coupled loosely as long as the atomic lattice planes (80) and the atomic lattice planes (40a) are in parallel with each other.

Fourth Embodiment

It should be noted that in the first and second embodiments, the analyzer crystals in use have predetermined functions and properties, such as transmission type (the transmission-type analyzer crystal (4a)) and reflection type (the reflection-type analyzer crystal (4b)).

Alternatively, an analyzer crystal sharable for both uses may be prepared, and adjusted in thickness in advance of an analysis so as to be usable as a transmission type and reflection type, thereby achieving a nondestructive analysis device usable for both types.

That is, when adjusted in thickness so as to satisfy both the thickness condition described in the first embodiment and the thickness condition described in the second embodiment, the analyzer crystal can be used for both the transmission type and reflection type.

Consequently, the ones of FIGS. 2 and 8, for example, can be offered as analysis devices usable for both types, not as the dedicated transmission-type analyzer crystal (4a) or the dedicated reflection-type analyzer crystal (4b).

Furthermore, for example, when the analyzer crystals are used as transmission type, the X-rays (3) from the object (2) are desirably made incident from obliquely above as in FIG. 2. When the analyzer crystals are used as reflection type, the X-rays (3) from the object (2) are desirably made incident from directly above as in FIG. 8(*a*) (though oblique incidence is also available in reflection type). This requires a configuration in which the collimator (9) or the asymmetric monochromator (8) can be irradiated with the incident X-rays (7) or the monochromatic parallel X-rays (1) in the directions as shown in FIGS. 2 and 8(*a*), and also the configuration that the X-ray detecting devices (10) can be arranged in the positions as shown in FIGS. 2 and 8(*a*).

Thus, when the analyzer crystals set to the foregoing thickness condition are used, selections between transmission type and reflection type can be made arbitrarily by simply changing the incident direction of the X-rays (3) from the object (2) and the like, thus achieving nondestructive analyses applicable for both types.

The present invention has the characteristics as described above. Hereinafter, practical examples will be given with reference to the accompanying drawings for the sake of further detailed description of the embodiments.

PRACTICAL EXAMPLES

Practical Example 1

Figure 12:
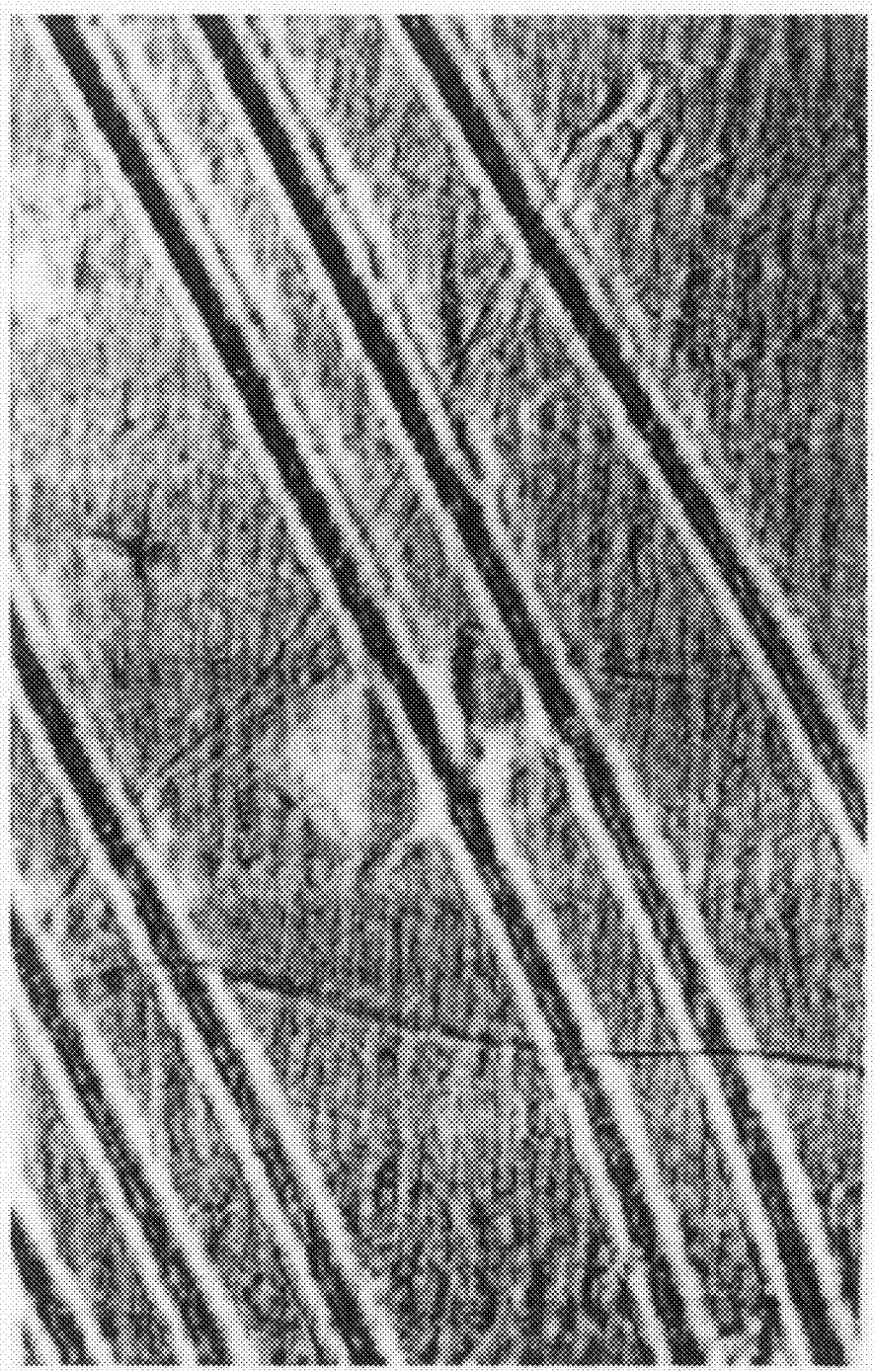
FIG. 12 is a diagram showing a practical example of nondestructive analysis by the invention of this application.

FIG. 12 shows an image of an object (2) made of 1.0-mm thick aluminum with 140-μm-diameter boron fibers embedded therein, the image being captured according to the embodiment of FIG. 2. A diamond-type silicon analyzer crystal of 4,4,0 reflection is used as the transmission-type analyzer crystal (4a). The thickness was adjusted to H that satisfies the relationships of the foregoing equations 1 and 3. As is evident from FIG. 12, an X-ray dark-field image (5) showing the boron fibers sharply was provided by the G-wave, i.e., the X-rays (42a) along the diffraction direction. Needless to say, an X-ray bright-field image (6) was provided at the same time.

Practical Example 2

Figure 13:
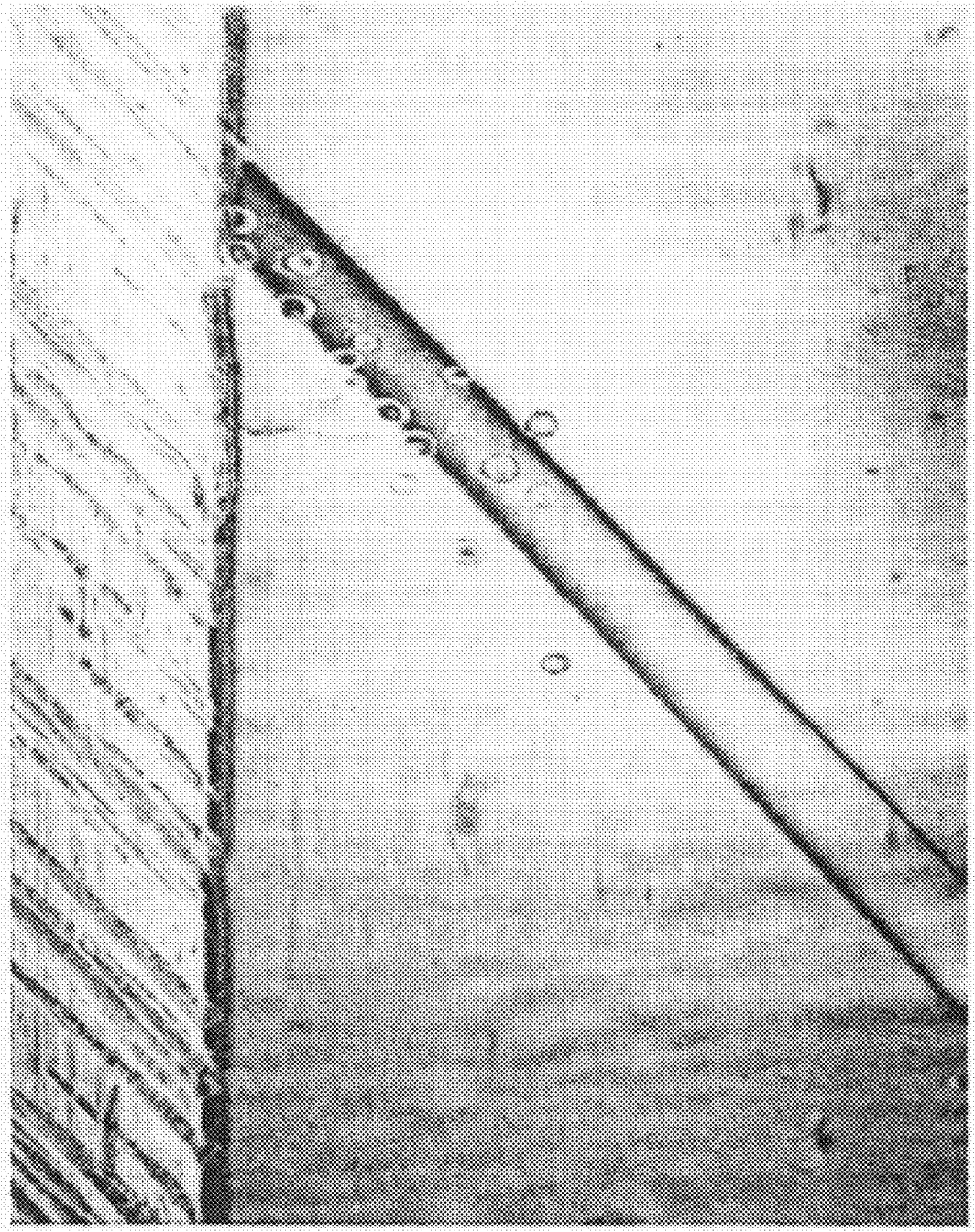
FIG. 13 is a diagram showing another practical example of nondestructive analysis by the invention of this application.

FIG. 13 shows an image of an object (2) made of 7.0-mm thick wax with 0.4-mm-diameter nylon fibers embedded therein, the image being captured according to the embodiment of FIG. 2. A crystal made of a diamond-type silicon analyzer crystal is used as the transmission-type analyzer crystal (4a). The thickness was adjusted to H that satisfies the relationships of the foregoing equations 1 and 3. As is evident from FIG. 13, an X-ray dark-field image (5) showing the nylon fibers sharply was provided by the G-wave, i.e., the X-rays (42a) along the diffraction direction. Needless to say, an X-ray bright-field image (6) was provided at the same time.

Practical Example 3

Figure 14:
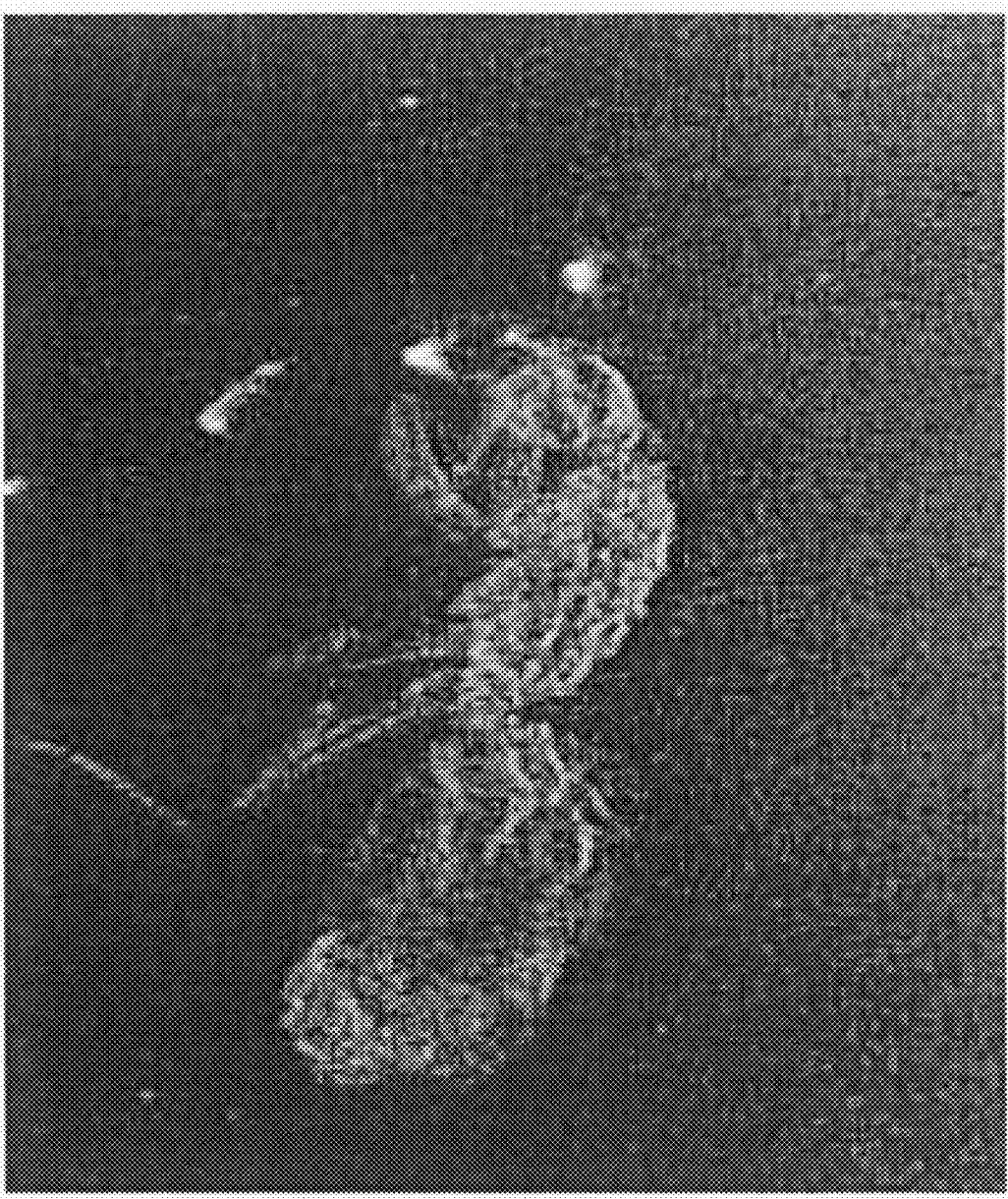
FIG. 14 is a diagram showing another practical example of nondestructive analysis by the invention of this application.

FIG. 14 shows an image of an object (2) made of amber containing an insect, the image being captured according to the embodiment of FIG. 2. A diamond-type silicon analyzer crystal was used as the transmission-type analyzer crystal (4a). The monochromatic parallel X-rays (1) displayed an energy of 35 keV. As is evident from FIG. 14, a sharp X-ray dark-field image (5) showing the insect was provided. Needless to say, an X-ray bright-field image (6) was provided at the same time.

Practical Example 4

Figure 15:
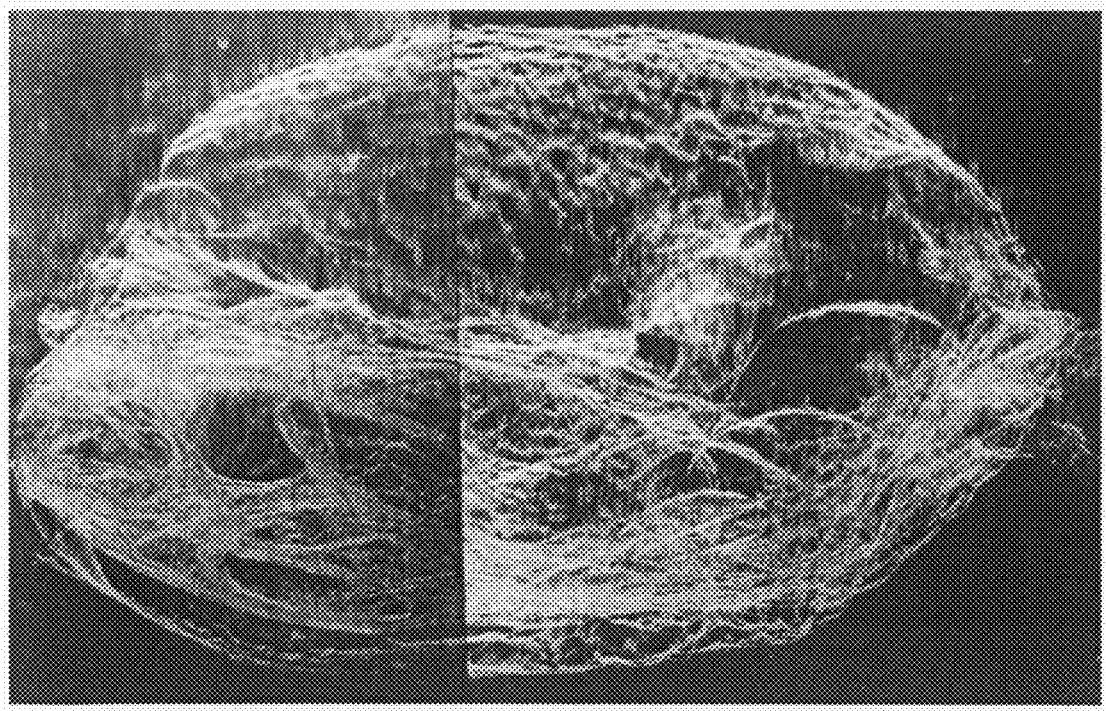
FIG. 15 is a diagram showing another practical example of nondestructive analysis by the invention of this application.

FIG. 15 shows an image of a dried fish as an object (2) to be analyzed, the image being captured according to the embodiment of FIG. 8. A silicon crystal of 4,4,0 reflection was used as the reflection-type analyzer crystal (4b). The thickness was set at 1 mm. As is evident from FIG. 15, an X-ray dark-field image (5) showing the dried fish sharply by means of transmission X-rays $I_T$ (41b) was provided. Needless to say, an X-ray bright-field image (6) was provided separately by reflection X-rays $I_B$ (42b). Obviously, the present invention is by no means limited to any of the foregoing examples, and various modifications may be made to details.

Note that the present invention can be easily practiced in the form of the foregoing methods or devices in accordance with the equations 1, 2, and 3 while using other electromagnetic waves or neutron beams, electron beams, or other corpuscular beams instead of the X-rays. As is the case with the X-rays, excellent nondestructive analyses can be performed by using the other electromagnetic waves or corpuscular beams. In this case, for example, transmitted corpuscular beams, refracted corpuscular beams, diffracted corpuscular beams, small angle scattering corpuscular beams, secondary corpuscular beams, and/or the like from the object (2) are made incident on the transmission-type analyzer crystal (4a) or the reflection-type analyzer crystal (4b). The corpuscular beams along the forward diffraction direction and the corpuscular beams along the diffraction direction from the transmission-type analyzer crystal (4a), or the transmitted corpuscular beams and the reflected corpuscular beams from the reflection-type analyzer crystal (4b), are detected by using corpuscular beams detecting devices instead of the X-ray detecting devices (10). Image creation can be performed by image processing equipment capable of image processing using the detecting data of corpuscular beams.

The electromagnetic waves other than X-rays ($10^{-3}$ nm to 10 nm) include gamma rays ($10^{-2}$ nm or shorter), ultraviolet rays (1 nm to 400 nm), visible rays (400 nm to 800 nm), and infrared rays (800 nm to 4000 nm). Any of these can be used to effect the above-described nondestructive analysis according to the invention of this application. Incidentally, the source of the names and wavelength bands of these electromagnetic waves is "electromagnetic waves" in "*Butsurigaku Jiten [Dictionary of Physics]*, the 4th Revision" (Baifukan, 1998). The names and wavelength bands of the electromagnetic waves seen in this source are not the only suitable ones, and any electromagnetic wave is applicable as long as it is capable of the above-described nondestructive analysis according to the invention of this application.

The invention of this application described above can provide even new comprehensive systems, such as inspection and processing systems, medical diagnostic systems, and status- and form-variation observing systems, which can analyze the structure and function of any kind of objects, including foods, drugs, medical diagnostic subjects, semiconductors, and organic and inorganic substances which have been impossible to elucidate or check by the conventional art, in a nondestructive manner with high contrast and high resolution (for example, at least on the order of several tens of micrometers or less). Consequently, in every field of application, it becomes possible to identify objects useful to that field out of various objects, and offer them as new products such as useful foods and useful drugs.

In particular, in the field of microscopic technologies in which significant advances of technical innovation have been seen, the invention of this application can be practiced to achieve high synergistic effects. For example, it is possible to identify and offer an object appropriate for a new drug out of any type of objects by elucidating the physiological status of the brain, liver, or the like of an animal, human being, or the like, elucidating the process and status of occurrence and development of cancer, and elucidating the cause-and-effect relationships among the process of occurrence and development of cancer, the status of form variations thereof, and medication.

Moreover, for structural analyses in the field of polymers such as a protein structural analysis, the combination with the structural analysis at an atomic structure level in X-ray diffraction analysis or the like makes it possible to design and offer a new drug, antibody, or the like through the analysis and elucidation in association with what the structure of the macroscopic form is like.

As has been detailed above, the invention of this application provides a new nondestructive analysis method and nondestructive analysis device by which high-contrast images of the internal structure of any kind of object, regardless of a living body/non-living body, crystal/amorphous, single member/composite member, solid/liquid, etc., can be easily obtained as an X-ray dark-field image and an X-ray bright-field image at one time. In particular, the X-ray image in the form of X-ray dark-field image, as compared to that of X-ray fluoroscopy not available heretofore, has a significant feature that the structure of the object to be analyzed can be analyzed with extremely high contrast, high precision, extreme visibility, and facility by a simple configuration. In addition, when the nondestructive analysis method and device of the invention of this application are used for nondestructive analysis, it also becomes possible to identify objects having useful operation, effect, and the like in a variety of fields, and provide them as new products or the like.

What is claimed is:

1. A nondestructive analysis method, comprising:
   irradiating an object with monochromatic parallel X-rays such that X-rays from the object are incident on a transmission-type analyzer crystal;
   obtaining an inside image of the object by X-rays emitted from the transmission-type analyzer crystal; and setting a thickness of the transmission-type analyzer crystal such that irradiation with the monochromatic parallel X-rays in the absence of the object results in a condition in which either one of (a) X-rays along a forward diffraction direction and (b) X-rays along a diffraction direction obtained by a dynamic diffraction operation by the transmission-type analyzer crystal have an intensity of nearly zero when compared to an intensity of other X-rays with respect to the monochromatic parallel X-rays; and wherein said obtaining step obtains at least one of an X-ray dark-field image and an X-ray bright-field image.

2. The method of claim 1, wherein said obtaining step obtains both an X-ray dark-field image and an X-ray bright-field image.

3. The method of claim 1, wherein said irradiating step comprises irradiating the object via an asymmetric monochromator having lattice planes parallel to those of the transmission-type analyzer crystal.

4. A nondestructive analysis method, comprising:

irradiating an object with monochromatic parallel X-rays such that X-rays from the object are incident on a transmission-type analyzer crystal;

obtaining an inside image of the object by X-rays emitted from the transmission-type analyzer crystal; and setting a thickness of the transmission-type analyzer crystal such that irradiation with the monochromatic parallel X-rays in the absence of the object results in a condition in which either one of (a) X-rays along a forward diffraction direction and (b) X-rays along a diffraction direction obtained by a dynamic diffraction operation by the transmission-type analyzer crystal have an intensity of nearly zero when compared to an intensity of other X-rays with respect to the monochromatic parallel X rays, wherein said irradiating step results in at least one of (a) the X-rays along the forward diffraction direction and (b) the X-rays along the diffraction direction being obtained from the X-rays from the object that are incident on the transmission-type analyzer crystal.

5. A nondestructive analysis method comprising:

irradiating an object with monochromatic parallel X-rays such that X-rays from the object are incident on an analyzer crystal, wherein the analyzer crystal is usable as both a transmission-type and a reflection-type analyzer crystal; and setting two different thicknesses of the analyzer crystal to satisfy two conditions including: (1) a thickness such that irradiation with the monochromatic parallel X-rays in the absence of the object results in a condition in which either one of (a) X-rays along a forward diffraction direction and (b) X-rays along a diffraction direction obtained by a dynamic diffraction operation by the analyzer crystal have an intensity of nearly zero when compared to an intensity of other X-rays with respect to the monochromatic parallel X-rays; and (2) a thickness such that X-rays from the object satisfy a diffraction condition and are transmitted by the dynamic diffraction operation of the analyzer crystal, wherein said irradiating step comprises one of irradiating the object such that the analyzer crystal is used as a transmission-type analyzer crystal and irradiating the object such that the analyzer crystal is used as a reflection-type analyzer crystal; and obtaining an inside image of the object by X-rays emitted from the analyzer crystal, wherein at least one of an X-ray dark-field image and an X-ray bright-field image are obtained from the analyzer crystal if the analyzer crystal is used as a transmission-type analyzer crystal, and wherein an X-ray dark-field image is obtained from the analyzer crystal if the analyzer crystal is used as a reflection-type crystal.

6. A non-destructive analysis method, comprising:

providing radiation selected from the group consisting of X-rays and neutron beams from a radiation source and using a pre-crystal device to generate monochromatic parallel radiation from the radiation source;

irradiating an object with the monochromatic parallel radiation such that the radiation from the object is incident on a transmission-type analyzer crystal, wherein atomic lattice planes of the pre-crystal device are fixed approximately parallel with atomic lattice planes of the analyzer crystal so as to use an angular analysis capability of the analyzer crystal;

wherein the transmission-type analyzer crystal has a thickness such that irradiation with the monochromatic parallel radiation in the absence of the object results in a condition in which either one of (a) radiation along a forward diffraction direction and (b) radiation along a diffraction direction obtained by a dynamic diffraction operation by the transmission-type analyzer crystal has an intensity of nearly zero when compared to an intensity of other X-rays with respect to the monochromatic parallel radiation;

obtaining at least one of (a) a dark-field image or a bright-field image inside the object along the forward diffraction direction and (b) a bright-field image or a dark-field image inside the object along the diffraction direction; and detecting the at least one of a dark-field image and a bright-field image with a radiation detecting device.

* * * * *